United States Patent [19]

Tsujita et al.

[11] Patent Number: 5,457,326
[45] Date of Patent: Oct. 10, 1995

[54] SURFACE INSPECTION APPARATUS OF SPHERICAL MATTER

[75] Inventors: Kazukiyo Tsujita; Osamu Michinishi; Kenichi Fujinami, all of Osaka, Japan

[73] Assignee: Daio Steel Ball Mfg. Co., Ltd., Osaka, Japan

[21] Appl. No.: 228,382

[22] Filed: Apr. 15, 1994

[30] Foreign Application Priority Data

| May 18, 1993 | [JP] | Japan | 5-139966 |
| Jun. 18, 1993 | [JP] | Japan | 5-172759 |
| Jun. 18, 1993 | [JP] | Japan | 5-172760 |
| Aug. 20, 1993 | [JP] | Japan | 5-228062 |

[51] Int. Cl.$^6$ .................................................. G01N 21/88
[52] U.S. Cl. ..................... 250/559.42; 356/237; 356/426
[58] Field of Search .................................. 250/571, 572, 250/560, 561, 562, 563; 356/237, 445, 446, 448, 244, 426, 428, 338, 371, 376, 398

[56] References Cited

U.S. PATENT DOCUMENTS

| 3,586,864 | 11/1971 | Brany et al. | 356/237 |
| 4,227,809 | 10/1980 | Satoh et al. | 356/446 |
| 4,259,013 | 3/1981 | Faxvog et al. | 356/237 |
| 4,398,825 | 8/1983 | Lewis | 356/237 |
| 4,555,635 | 11/1985 | Yoshida | 250/572 |
| 4,960,332 | 10/1990 | Földi et al. | 356/237 |
| 5,012,116 | 4/1991 | Russell | 250/572 |
| 5,309,229 | 5/1994 | Stolz et al. | 356/237 |

Primary Examiner—Edward P. Westin
Assistant Examiner—John R. Lee
Attorney, Agent, or Firm—Birch, Stewart, Kolasch & Birch

[57] ABSTRACT

A surface inspection apparatus of steel balls and other spherical matter which enables the detection of defects on the surface of the spherical matter placed on a holder 2 by means of an inspection unit 1 comprising a proper number of electromagnetic sensors. The holder 2 possesses a rotatable support 20, and an auxiliary support 23 for supporting the spherical matter together with the support 20. The support 20 possesses a receiving groove 3 formed annularly along the rotating spherical peripheral surface, and this receiving groove 3 can accommodate the vicinity of the bottom of the spherical matter, and by the rotation of the support 20, the spherical matter can be rolled within the receiving groove 3 so that the direction of the spherical matter can be changed, thereby automatically changing the inspection position of the spherical matter. As a result, the surface inspection precision of steel balls or other spherical matter can be enhanced, and product qualification can be determined automatically and efficiently.

4 Claims, 19 Drawing Sheets 5,457,326

SURFACE INSPECTION APPARATUS OF SPHERICAL MATTER

BACKGROUND OF THE INVENTION

The present invention relates to a surface inspection apparatus of spherical matter such as steel balls, other metal balls, ceramic balls, spherical stones, plastic balls and the like.

Hitherto, for surface flaw detection or roundness inspection of spherical matter such as steel balls, generally, light was emitted to the surface of the spherical matter, and the reflected light was detected by a photo sensor.

In such detection, there has been a demand for detection of plural positions on the surface of spherical matter to enhance the precision of inspection.

To meet such demand, it has been possible to inspect plural positions by one inspection job by using multiple sensors and disposing sensors at different positions on the spherical matter.

If, however, it is desired to inspect each position on the surface of the spherical matter within a wide range by using multiple sensors, sensors cannot be disposed at the bottom of the spherical matter, for example, because it is supported on a holder or a table, which gives rise to the necessity of inspecting again by turning the spherical matter upside down after inspecting the upper hemisphere of the spherical matter. If such job is done manually each time, it is impossible to inspect a large quantity of spherical samples efficiently. It is hence a primary object of the invention to solve such problems.

BRIEF SUMMARY OF THE INVENTION

A surface inspection apparatus of spherical matter according to a first embodiment comprises an inspection unit 1 possessing electromagnetic sensors such as photo sensors, and a holder 2 for mounting steel balls or other spherical matter, and is constituted as follows.

The inspection unit 1 detects surface defects of spherical matter put on the holder 2 by a proper number of electromagnetic sensors. The holder 2 possesses a rotatable support 20 and an auxiliary support 23 for supporting the spherical matter together with the support 20. The support 20 possesses a receiving groove 3 formed in an annular form along its rotating peripheral surface, and this receiving groove 3 can accommodate the vicinity of the bottom of the spherical matter, and the spherical matter is rolled within the receiving groove 3 by the rotation of the support 20, so that the direction of the spherical matter can be changed. The auxiliary support 23 is formed separately from the support 20, and disposed near the support 20, and is designed to support that portion of the spherical matter exposed from the receiving groove 3, and holding the spherical matter at a specific position.

In a surface inspection apparatus of spherical matter in a second invention embodiment, which is similar to the first invention, the auxiliary support 23 possesses a rotating body 230 in the position contacting with the spherical matter. This rotating body 230 can rotate the spherical body in a different direction from the rotating direction of the support 20.

Furthermore, a surface inspection apparatus of spherical matter in a third embodiment comprises an inspection unit 1 possessing electromagnetic sensors such as photo sensors, and a holder 2 for mounting steel balls or other spherical matter, and is constituted as follows.

That is, the inspection unit 1 detects surface defects of spherical matter put on the holder 2 by a proper number of electromagnetic sensors. The holder 2 possesses a rotatable first support 21, a rotatable second support 22, and an auxiliary support 23 for supporting the spherical matter together with the first support 21 and second support 22. The first support 21 and second support 22 can rotate at mutually different rotating speeds.

In a surface inspection apparatus of spherical matter in a fourth embodiment, which is similar to the third embodiment, the auxiliary support 23 possesses a rotating body 230 at a position contacting with the spherical matter, and the rotating body 230 provides the spherical matter with a torque in a proper direction.

A surface inspection apparatus of spherical matter in a fifth invention comprises a feed unit 4 for feeding spherical matter such as steel balls, a transfer unit 26 for transferring the spherical matter supplied from the feed unit 4 for a specific distance, an inspection unit 1 for inspecting the surface of the spherical matter on the transfer unit 24 by using electromagnetic wave such as beam of light, and a sorting unit 5 for sorting the spherical matter sent from the transfer unit 26 depending on the result of inspection by the inspection unit 1. The transfer unit 26 has a first support 21 of nearly columnar shape forming the a transfer route for spherical matter, and a second support 22 possessing a longitudinal width at least nearly same as the first support 21, formed as being extended from the feed unit 4 side to the sorting unit 5 side. The first support 21 rotates about the symmetrical axis of its own column, and a guide groove 300 extending spirally is formed on its circumference from the end part of the feed unit 4 side to the end part of the sorting unit 5 side. The guide groove 300 transfers and guides the spherical matter from the end part of the feed unit 4 side to the end part of the sorting unit 5 side, and sequentially varies the rotating direction of the spherical matter itself in the midst of transfer. In the guide groove 300, plural transfer rest positions 301 . . . at lead angle of nearly zero are formed. As the second support 22 is disposed nearly parallel, adjacently to the first support 21, a narrow gap 350 is formed against the first support 21, and by mounting the spherical matter using the narrow gap 350 as transfer route, the spherical matter is supported in the process of transfer by making use of the force of the spherical matter M falling into the narrow gap 350. The inspection unit 1 possesses plural electromagnetic sensors 10 such as photo sensors, and the individual sensors 10 are disposed near the first support 21 along the longitudinal direction of the first support 21. The sensors 10 are positioned at proper mutual intervals, and are designed to inspect the surface of the spherical matter staying in the individual rest positions 301 of the guide groove 300. The sorting unit 4 sorts by judging approval or rejection depending on the result of inspection obtained in each inspection unit 1 for every spherical matter.

In the apparatus of the first embodiment employing the above means, the spherical matter contained in the receiving groove 3 of the support 20 is rolled within the receiving groove 3 by the rotation of the support 20, and the direction of the spherical matter is changed, so that the inspecting position of the spherical matter can be changed automatically.

In the apparatus of the second embodiment, since the spherical matter can be rotated in a different direction from the rolling direction of the spherical matter by the support 20, all positions can be inspected uniformly without deviating the inspecting positions of the spherical matter, regardless of the quantity and location of the electromagnetic sensors of the inspection unit 1.

In the apparatus of the third embodiment, the first support 21 and second support 22 for composing the holder 2 to support the spherical matter can be rotated at mutually different rotating speeds, and therefore the mounted spherical matter can change the rotating direction in multiple directions, not limited to one direction only. Therefore, the surface of the spherical matter can be inspected uniformly at multiple angles.

In the apparatus of the fourth embodiment, since the rotating body 230 having the auxiliary support 23 can provide the spherical matter with a torque in the third embodiment, it is possible to convert the direction of the inspecting position of the spherical matter more finely, in addition to supply of torque to the spherical matter by the first support 21 and second support 22.

In the apparatus of the fifth embodiment, the guide groove 300 extending almost spirally is formed in the first support 21 of the transfer unit 26 interposed between the feed unit 4 and sorting unit 5, and therefore the spherical matter supported by the first support 21 and second support 22 is guided by the guide groove 300 contacting therewith by the rotating of the first support 21, and is transferred from the feed unit 4 side to the sorting unit 5 side, and is rotated sequentially in different directions. In the guide groove 300, the sensor 10 is disposed nearby and a plurality of transfer rest positions 301 nearly at lead angle of zero are formed, and the spherical matter standing still can be inspected at individual transfer rest positions 301, so as to be inspected securely at the sensor position. Together with this, as mentioned above, as being guided by the spiral guide groove 300, the spherical matter is sequentially changed in the rotting direction while passing through individual transfer rest positions 301, so that different positions of the spherical matter can be securely inspected by the sensors 10, thereby notably enhancing the precision inspection of each spherical matter.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein.

DETAILED DESCRIPTION OF THE PREFERRED EMBODIMENTS

Figure 1:
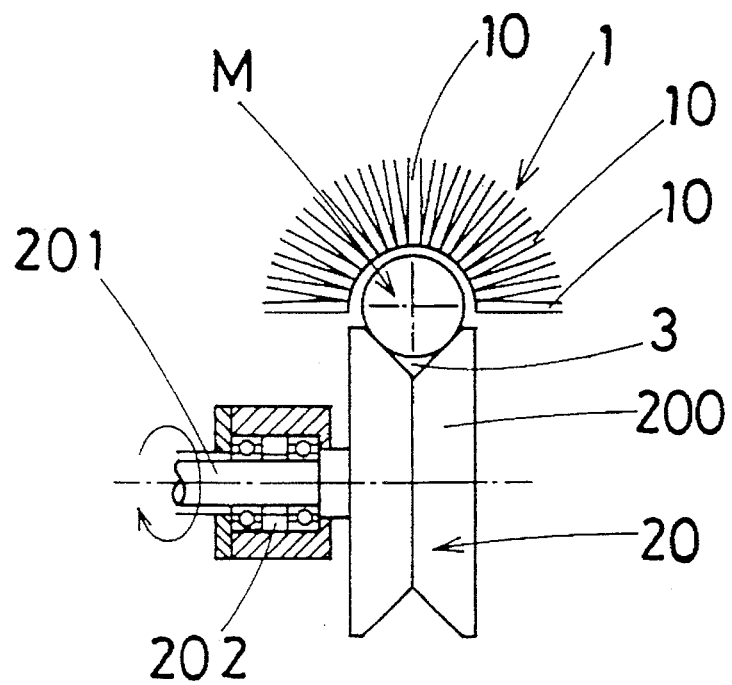
FIG. 1 is a partially cut-away front view showing an embodiment of the invention.

Referring now to the drawings, some of the embodiments of the invention are described specifically below. FIG. 1 shows an embodiment of the invention.

As shown in FIG. 1, the surface inspection apparatus of spherical matter such as steel balls of the invention is an apparatus usable in inspection of the surface of spherical matter M composed of steel ball, other metal ball, ceramic ball, spherical stone, plastic ball, or other material, and comprises an inspection unit 1 having electromagnetic sensors such as photo sensors, and a holder 2 for mounting the spherical matter M.

The composition of each component is sequentially described below.

The inspection unit 1 is capable of inspecting defects on the surface of spherical matter M mounted on the holder 2 by means of a proper number of electromagnetic sensors.

More specifically, it is formed separately from the holder 2 mentioned below, and is disposed above the holder 2.

The inspection unit 1 possesses plural photo sensors 10. The sensors 10 emit light to the object of inspection, and receive the reflected light to inspect the surface.

Figure 3:
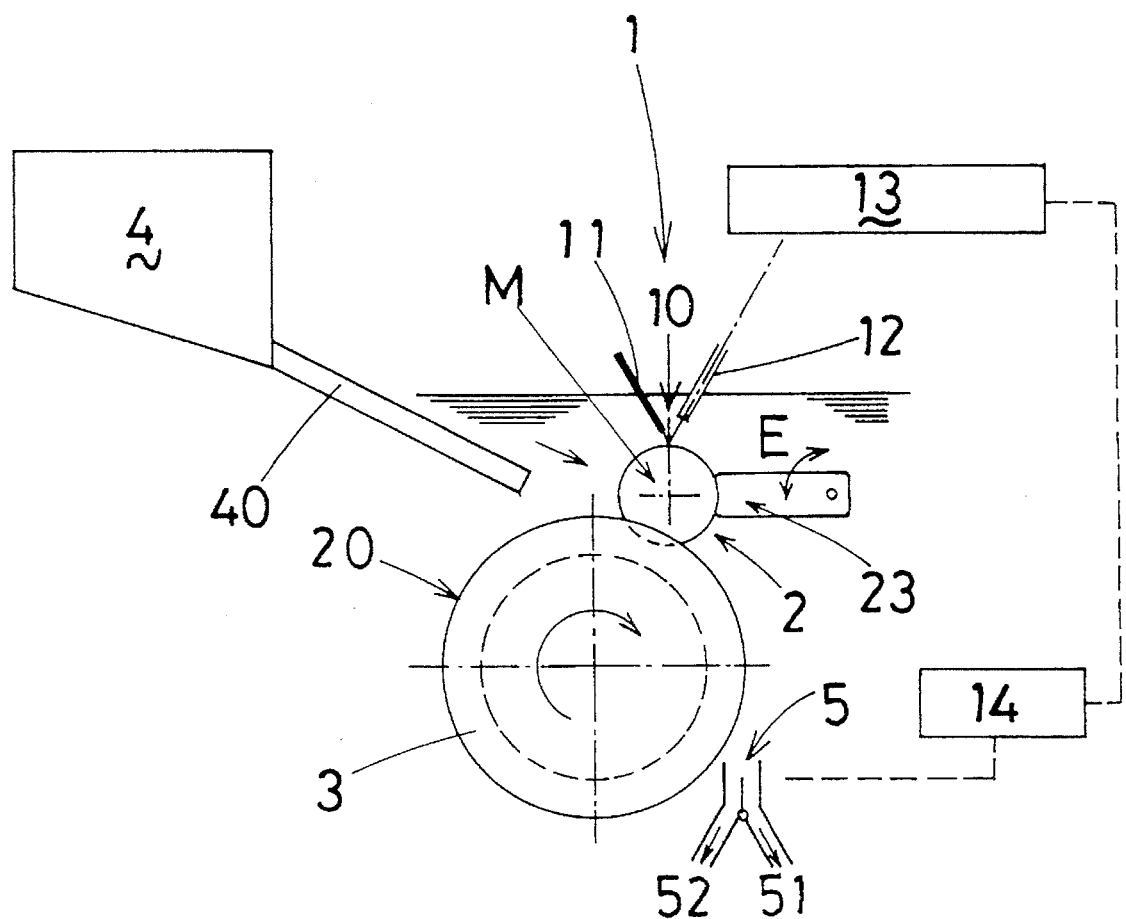
FIG. 3 shows general schematic side vies of the embodiments of the invention.

As such photo sensor 10, a projector 11 and a receiver 12 may be formed (integrated) into a unit, or the projector 11 and receiver 12 may be installed separately (FIG. 3).

In the embodiment shown in FIG. 1, the photo sensors 10 are disposed radially, but it is also possible to execute in other configuration.

The photo sensors 10 may be also realized by those designed to inspect the surface by using electromagnetic waves other than ordinary visible rays of light.

The number of sensors 10 to be disposed is not limited to the shown example, but it is possible to execute if more than or smaller than the shown number.

The individual sensors 10 may be formed in a small size as far as possible and the interval of the adjacent sensors 10, 10 may be be set small in order to increase the number of sensors 10 to be installed, so that the number of positions and the scope to be inspected once by the inspection unit 1 may increase, which contributes to efficiency and effect of inspection.

The holder 2 possesses a rotatable support 20, and an auxiliary support 23 capable of supporting the spherical matter M together with the support 20. Each constituent member of the holder 2 is explained sequentially below. The support 20 possesses a disk-shaped rotary part 200, a rotary shaft 201, and a bearing 202.

The disk-shaped rotary part 200 possesses a receiving groove 3 formed annularly along the circumference. This receiving groove 3 is at a position withdrawn from the surface of the rotary part 200 as shown in FIG. 1.

Figure 12:
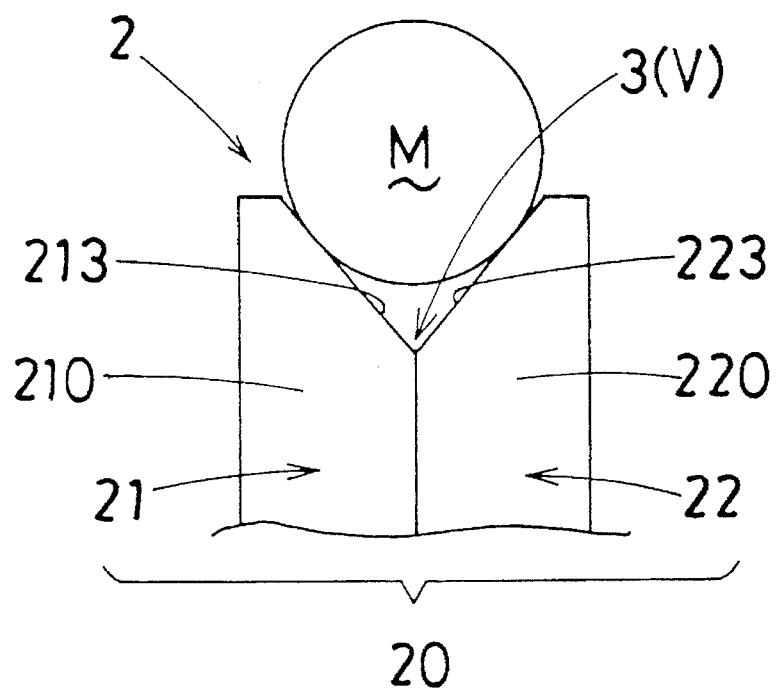
FIG. 12 is an essential front view of the above embodiment of the invention.

The receiving groove 3 receives the vicinity of the spherical matter M (FIG. 12). In FIG. 1, the receiving groove 3 is shown in withdrawn position in a form of V in sectional view, but such shape is not limited, and the receiving groove 3 may be formed in other shapes, such as U-form in sectional view. Or, when forming the receiving groove 3 in an approximately V-form in sectional view, the inclination angle of the both inner walls may be set larger or smaller than shown in the diagram, and the depth may be also different from the shown size. The receiving groove 3 may be formed in a proper size depending on the size of the spherical matter M.

Concerning the form of the holder 2 and receiving groove 3, other embodiments are described below.

In the above embodiment, the rotary shaft 200 has one end fixed in the middle of the rear end surface of the rotary part 200 (in FIG. 1, the right side of the rotary part 200 is the front end, and the left side is the rear end). The rotary shaft 200 is designed to rotate the rotary pat 200 by the torque obtained from the torque feed means such as motor.

Such torque feed means is connected directly to the rotary shaft 201, or the torque may be obtained through gear or pulley and belt.

The bearing 202 is to rotatably support the rotary shaft 201. In the drawing, the constitution for supporting the bearing 202 is omitted in order to avoid complication of the drawing.

Figure 2:
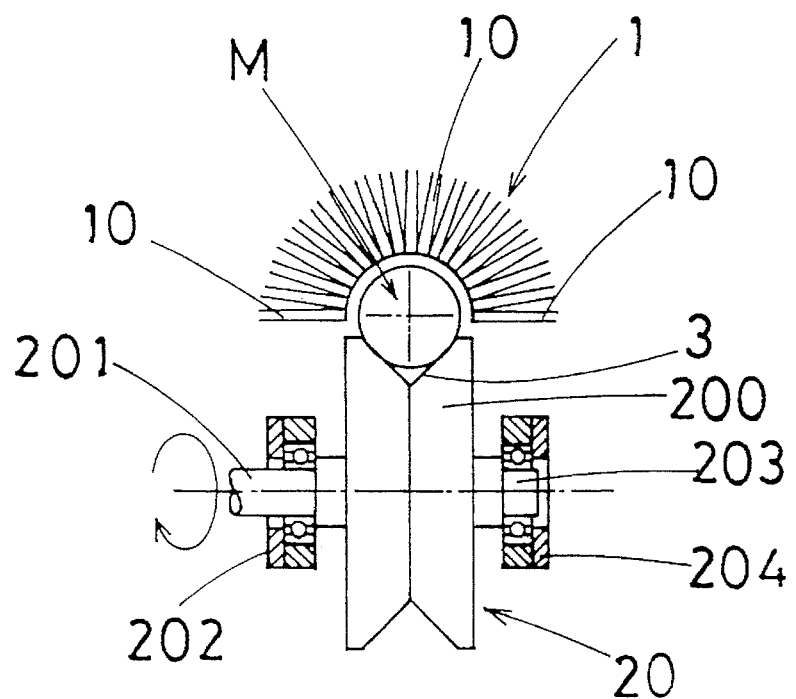
FIG. 2 is a partially cut-away front view showing other embodiment of the invention.

Or, as shown in FIG. 2, a projecting shaft 203 as an extension of the rotary shaft 201 is also provided in the middle of the front end surface of the rotary part 200, and a bearing 204 for freely fitting the projecting shaft 203 is provided, so that it may be effective for supporting the rotary part 200 from both sides.

The auxiliary support 23 is a tubular body extending in the horizontal direction as shown in FIG. 3, and the rear end is fixed to the device, while the front end (the left side in FIG. 3 is the front end, and the right side is the rear end) contacts with the lateral surface of the spherical matter M, thereby preventing the spherical matter M from dropping out of the receiving groove 3. Thus, the spherical matter M is held at specific position by the support 20 and auxiliary support 23.

By the rotation of the support 20, the spherical matter M rolls within the receiving groove 3, and its direction is changed relatively to the inspection unit 1.

Figure 4:
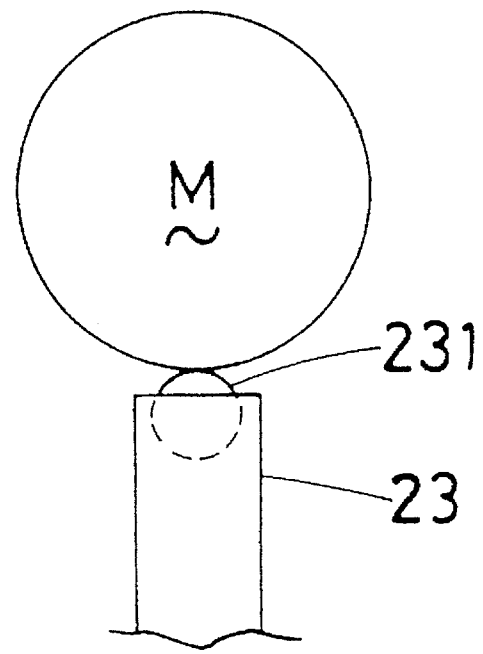
FIG. 4 is an essential magnified view showing a different embodiment of the invention.

When the front end of the auxiliary support 23 is provided with a bearing 231 as shown in FIG. 4, the rotation of the spherical matter M by the support 20 can be effected smoothly, and it is very effective.

Figure 5:
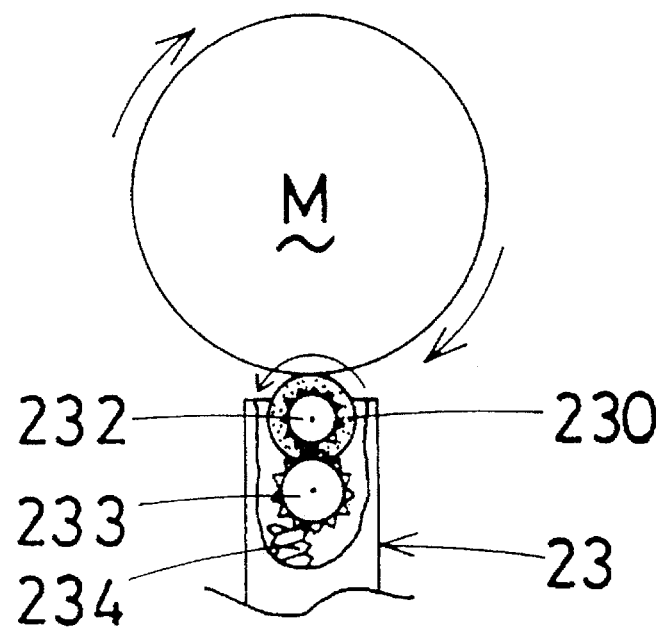
FIG. 5 is a partially cut-away essential magnified view showing a different embodiment.

Moreover, the auxiliary support 23 has a rotating body 230 such as rubber roller at its front end as shown in FIG. 5, and this rotating body 230 obtains a torque from a motor or the like (different from the one for feeding torque to the rotary shaft 211, not shown) through transmission means of worm gear 234 or the like, and rotates the spherical matter M in a direction different from the torque given by the support 1 to the spherical matter M, which is also effective.

The constitution for rotating the rotating body 230 is not limited to the one shown in FIG. 5, and it may be realized by the one for rotating by using pulley or pulley belt, or the one for obtaining torque by other method.

When employing the constitution of the gear or the like, it is not limited to the one in FIG. 5, but it may be realized by employing gears of other configuration or different quantity, or gears of other types.

As for the rotating body 230 itself, it is not limited to the rubber roller, but other material or member may be used.

Figure 6:
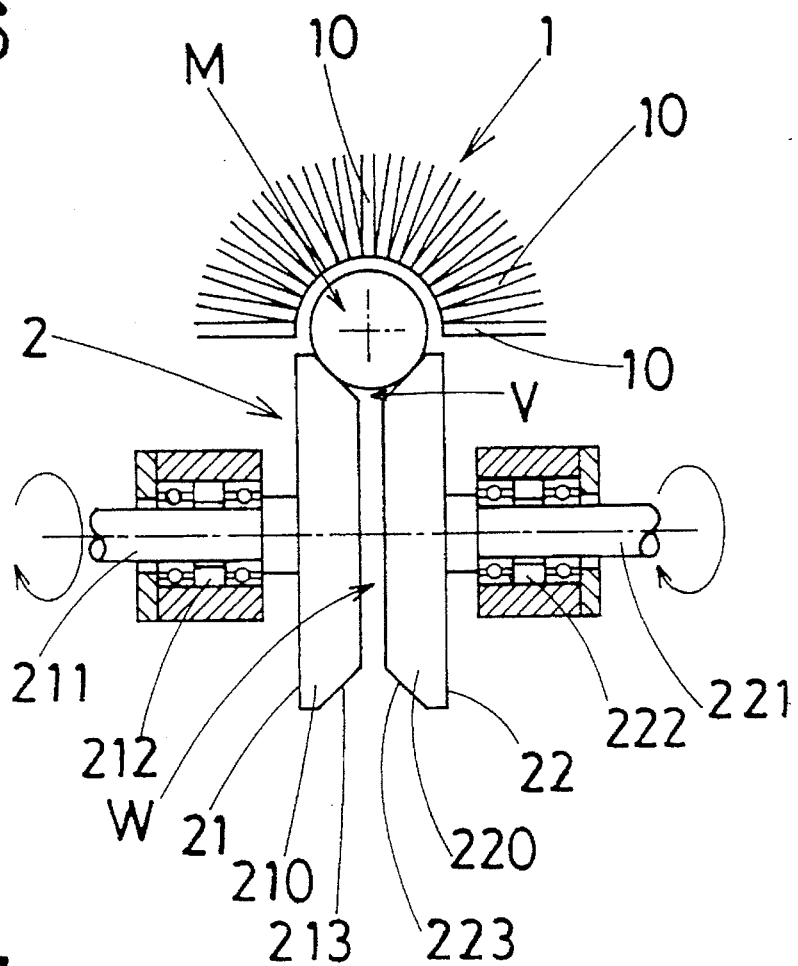
FIG. 6 is a partially cut-away front view showing an embodiment of the invention.

In the above embodiment, the holder 2 is composed of the support 20 and auxiliary support 23, but as shown in FIG. 6, the holder 2 may be composed of a rotatable first support 21, a second support 22 rotatably independently of the rotation of the first support 21, and an auxiliary support 23.

More specifically, the support 2 consists of, in the embodiment shown in FIG. 6, the first support 21 for composing the left part and the second support 22 for composing the right part, and the first support 21 and second support 22 are formed to rotate independently. Therefore, the support 2 in the foregoing (for example shown in FIG. 1) embodiment may be regarded to be a combined form of the first support 21 and the first support 21 to rotate in unison.

In this embodiment, the first support 21 and second support 22 are supposed to have a nearly same diameter of rotation, but the invention may be realized if the diameters of the first support 21 and second support 22 re different as far as capable of supporting the spherical matter and feeding rotary force to the spherical matter M.

These supports 21, 22, 23 support so that the spherical matter M may not drop out.

Hereinafter the constituent members of the holder 2 of the embodiment shown in FIG. 6 are explained.

The first support 21 possesses a rotary part 210, a rotary shaft 211 and a bearing 212. The rotary part 210 is formed in a disk shape, and a tapered abutting surface 213 is formed on the circumference. In the center of the back side 214 of the rotary part 210, one end of the rotary shaft 211 is fixed. The rotary shaft 211 is rotate the rotary part 210 by the torque obtained from torque feed means such as motor (not shown). The bearing 212 rotatably supports the rotary shaft 211 (the support means of the bearing 212 itself is not shown in order to avoid complication of drawing).

The second support 22, same as the first support 21, possesses a rotary shaft 221 and a bearing 222. The rotary pat 220 is formed in a disk shape, and a tapered abutting surface 223 is formed on the circumference. In the center of the back side 224 of the rotary part 220, one end of the rotary shaft 221 is fixed. The rotary shaft 221 is rotate the rotary part 220 by the torque obtained from torque feed means such as motor (not shown). The bearing 222 rotatably supports the rotary shaft 221 (the support means of the bearing 222 itself is not shown in order to avoid complication of drawing).

As shown in FIG. 6, the first support 21 and second support 22 are disposed so that the both rotary shafts 211, 212 may be positioned on a same straight line, and that the disk surfaces of the two rotary parts 210, 220 may confront each other. The both abutting surfaces 213, 223 of the first support 21 and second support 22 form a bottom V in a V form in sectional view, and the spherical matter M is put on this bottom V. The slope angle of the abutting surfaces 213, 223 for forming the bottom B may be changed properly depending on the size of the spherical matter M. The interval W between the two rotary parts 210, 220 may be changed properly depending on the size of the spherical matter M to be mounted. The abutting surfaces 213, 223 are not limited to taper shape (conical form or truncated conical form), but may be formed in different shapes. Therefore, the bottom V formed by the abutting surfaces 213, 223 is not limited to a V section, but may be formed in other shape depending on the shape of other abutting surfaces 213, 223.

Herein, the bottom V in V section formed by the abutting surfaces 213, 223 corresponds to the receiving groove 3 in the foregoing embodiment (for example as shown in FIG. 1). Therefore, other embodiments of the bottom V are explained together with other embodiments of the shape of the receiving groove 3 in FIG. 1.

The spherical matter M is securely supported at three points by the abutting surfaces 213, 223 and the auxiliary support 23.

In this constitution, the respective rotary parts 210, 220 of the first support 21 and second support 22 rotate at different speeds, and the rotating direction of the spherical matter M may be changed. By adjusting the difference in rotating speed of the rotary parts 210, 220, the change of the rotating direction of the spherical matter M is adjusted, and the most efficient change of rotating direction of the spherical matter M may be set.

When rotating the first support 21 and second support 22 at different rotating speeds, as mentioned above, the drive systems (motors, etc.) of the first support 21 and second support 22 may be composed separately, so that the constitution may be simplified. Otherwise, using one (common) motor for feeding torque, plural gears with different gear ratios, or plural pulleys and belts with different diameters may be employed in the driving force transmission system, that is, by constituting them through the motor and individual rotary shafts 211, 221, the rotating speeds of the first support 21 and second support 22 may be varied (not shown).

The difference in rotating speed can be changed depending on necessity. The rotation is not limited to one revolution or more, but half rotation or quarter rotation or other rotation of small angle may be also included in the concept of rotation as far as the inspection is done sufficiently.

Figure 7:
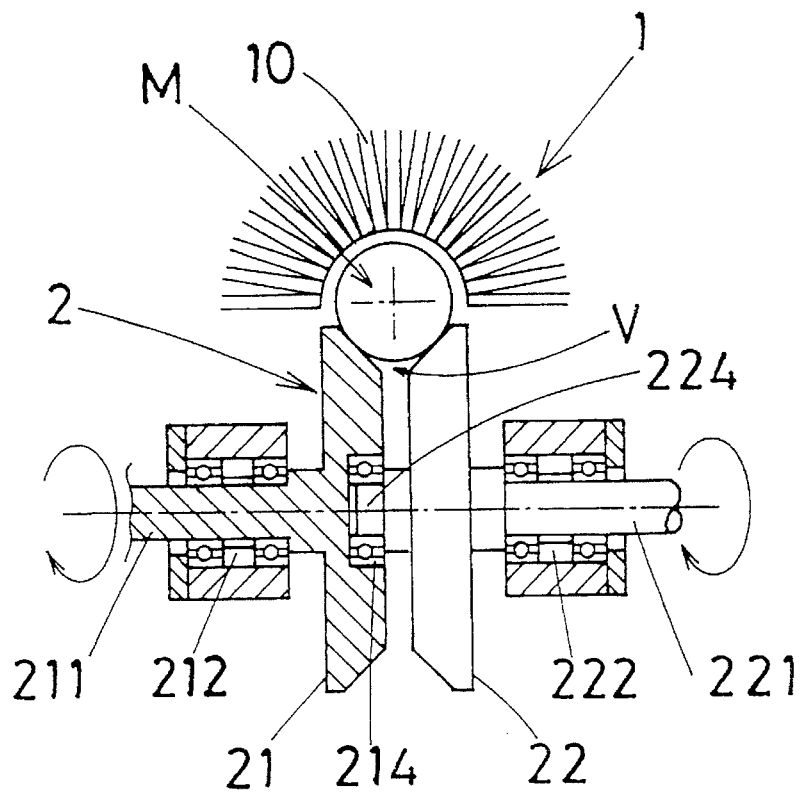
FIG. 7 is a partially cut-away front view showing a different embodiment of the invention.
Figure 8:
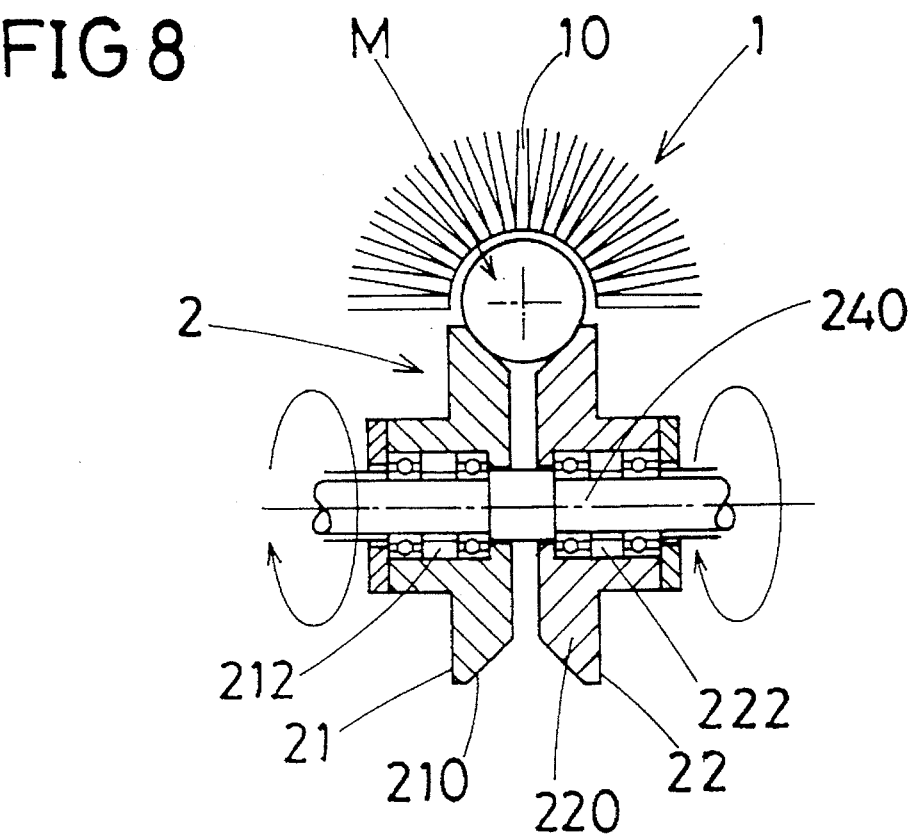
FIG. 8 is a partially cut-away front view showing a different embodiment of the invention.
Figure 9:
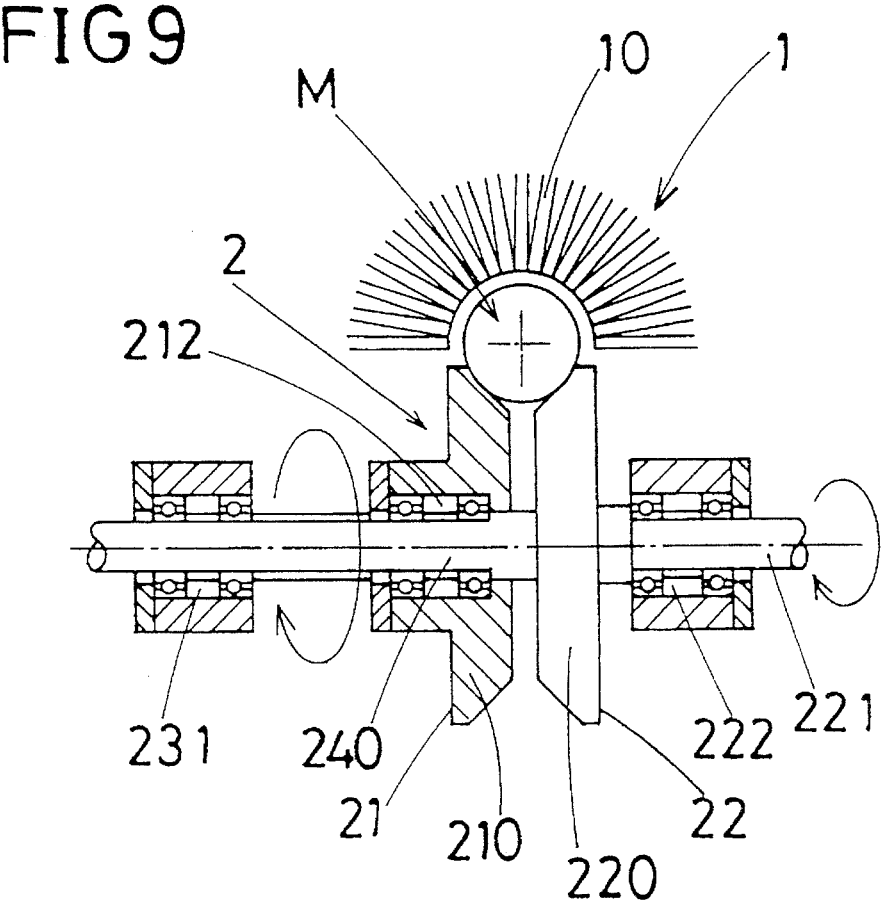
FIG. 9 is a partially cut-away front view showing a different embodiment of the invention.

The driving means of the first support 21 and second support 22 or the driving force transmitting means are further illustrated in other embodiments in FIGS. 7, 8 and 9.

What is shown in FIG. 7 differs from the embodiment shown in FIG. 6, and the first support 21 and second support 22 are not in contact-free state. More specifically, a bearing 214 is formed in the center of the surface of the first support 21, and a projecting shaft 224 as an extension of the rotary shaft is formed in the center of the surface of the second support 22, and this projecting shaft 224 is rotatably incorporated in the bearing 214. By thus constituting, the first support 21 may be partly responsible for support of the second support 22 without being blocked of its own rotation.

What is shown in FIG. 8 is characterized by free fitting of the first support 21 and second support 22 on one rotary shaft 240. More particularly, in the first support 21, the rotary part 210 and bearing 212 are integrally formed, while, in the second support 22, the rotary part 220 and bearing 222 are integrally formed. The supports 21, 22 are free to rotate on the shaft 240, and both first support 21 and second support 22 are composed so as to receive supply of torque directly from each other (the torque feed means is omitted to avoid complication of the drawing).

What is shown in FIG. 9 is a compound type of the embodiment shown in FIG. 6 or FIG. 7 and the embodiment shown in FIG. 8.

In detail, in the first support 21, the rotary pat 210 and bearing 212 are formed integrally, and are composed to be free to rotate on the shaft 240. The first support 21 rotates as torque is directly supplied from the other (the transmission means is omitted to avoid complication of drawing). In the second support 22, on the other hand, the rotary part 220 and rotary shaft 221 are integrally formed, and other bearing 222 is provided. The rotary shaft 221 is united with the shaft 240 (one is the extension of the other), and it is designed to rotate the rotary part 220 by supply of torque from the other.

In the embodiment shown in FIG. 9, an auxiliary bearing 231 is provided separately to stabilize rotation.

Referring to FIG. 10 through FIG. 16, other embodiments of the holder 2 (receiving groove 3 or abutting surfaces 213, 223) are described below.

Figure 10:
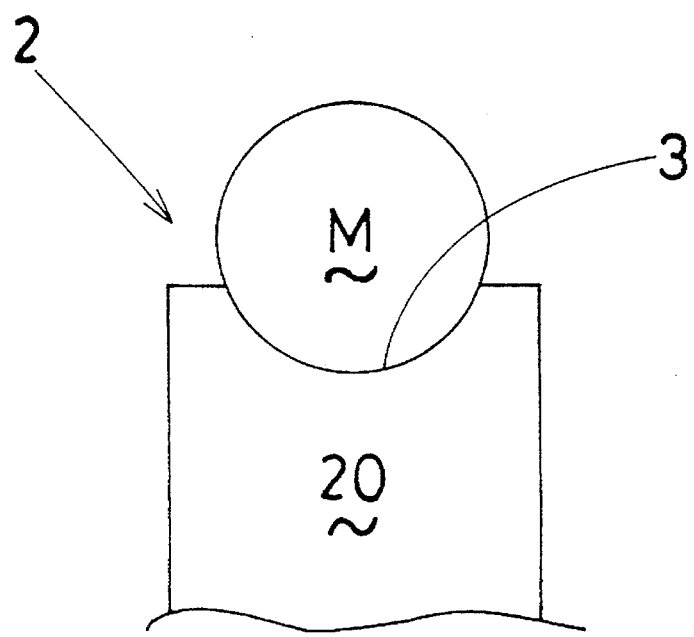
FIG. 10 is an essential front view showing a different embodiment of the invention.

What is shown in FIG. 10 is similar to the embodiment in FIG. 1 or FIG. 2, in which the internal sectional shape of the receiving groove of the support 20 for supporting the spherical matter M is shaped in an arc form or in a form along the spherical matter.

Figure 11:
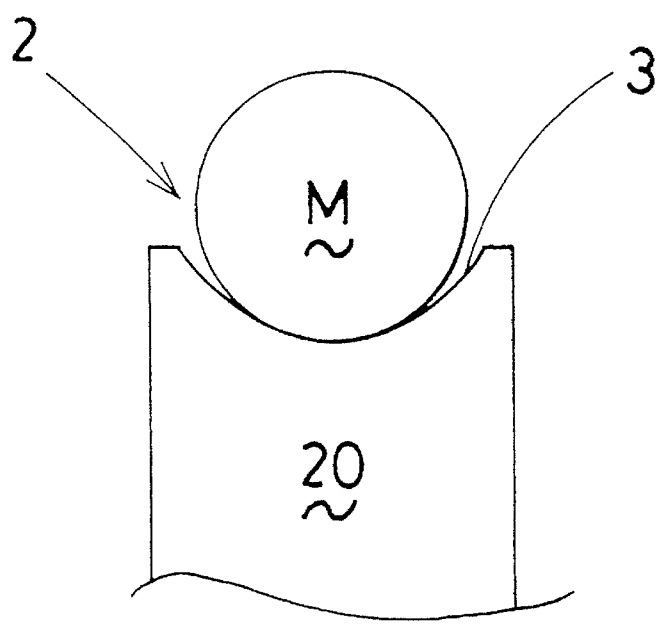
FIG. 11 is an essential front view showing a different embodiment of the invention.

Besides, as shown in FIG. 11, it is also possible to realize if the internal sectional shape of the receiving groove 3 of the support 20 for supporting the spherical matter M is not a perfect arc along the shape of the spherical matter M.

Other embodiments are further described below. The following embodiments are realized in both the type shown in FIG. 1 or FIG. 2, that is, the constitution in which the first support 21 and second support 22 are integrated (hereinafter called type A) as in the embodiment shown in FIG. 6 (or FIG. 7, 8 or 9), and the type shown in FIG. 6 in which the member corresponding to the support 20 in FIG. 1 is composed of the first support 21 and second support 22, and these supports 21, 22 rotate separately (type B).

For the simplicity of explanation, herein, in type A, same as in type B, the support 20 is composed of the first support 21 and second support 22, and the receiving groove 3 is supposed to be composed of the abutting surfaces 213, 223 possessed by the both supports 21, 22 (therefore, the receiving groove 3 corresponds to the bottom V; see FIG. 12). In the case of type A, it may be supposed that the first support 21 and second support 22 are formed in one body.

Figure 13:
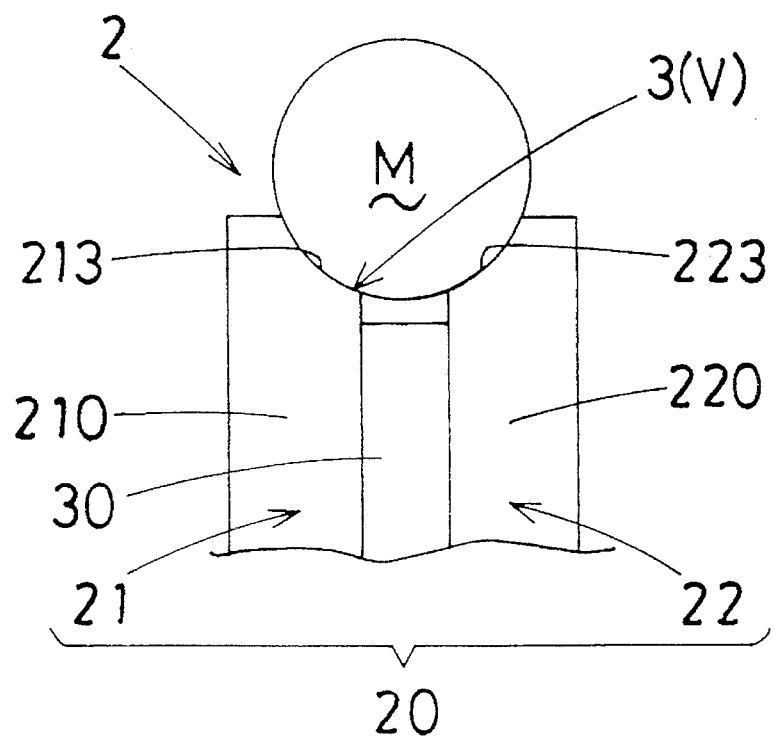
FIG. 13 is an essential front view showing a different embodiment of the invention.

First, in the embodiment shown in FIG. 13, the first support 21 and second support 22 are disposed at a proper interval. In the abutting surfaces 213, 223, same as the embodiment in FIG. 10, the sectional shape along the spherical matter M is respectively formed on an arc.

Numeral 30 is a spacer in disk form or shaft form for maintaining the interval between the first support 21 and second support 22. The spacer 30 is formed integrally with the first support 21 and second support 22 in the case of type A. In the case of type B, the spacer 30 may be executed if independent from both the first support 21 and second support 22 (free from effects of rotation of both), or if attached to either the first support 21 or the second support 22, or if rotating together with the first support 21 and second support 22.

Figure 14:
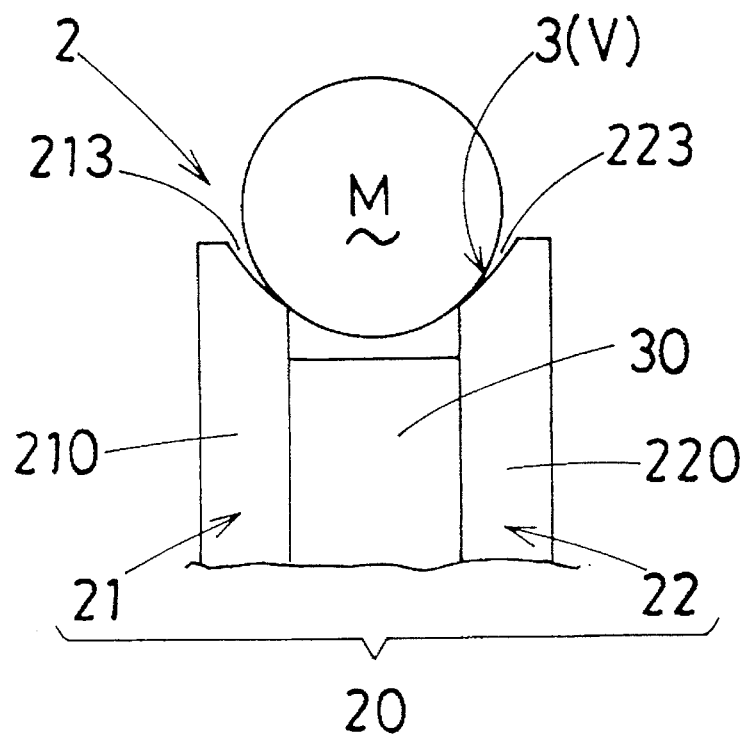
FIG. 14 is an essential front view showing a different embodiment of the invention.

As shown in FIG. 14, the abutting surfaces 213, 223 may be merely formed in an arc, not formed completely along the spherical matter M. The embodiment shown in FIG. 14 is nearly same as the one shown in FIG. 13 in constitution except for the abutting surfaces 213, 223. In FIG. 14, however, the spacer 30 is broader in width (the lateral width in FIG. 14) than the one shown in FIG. 13, but the dimensions such as the width of the spacer 30 may be changed as required. In type B, incidentally, when the constitution shown in FIG. 13 or FIG. 14 is applied, it is also possible to keep an interval of the first support 21 and second support 22 without using the spacer 30. This is also possible in other embodiments described below.

Figure 15:
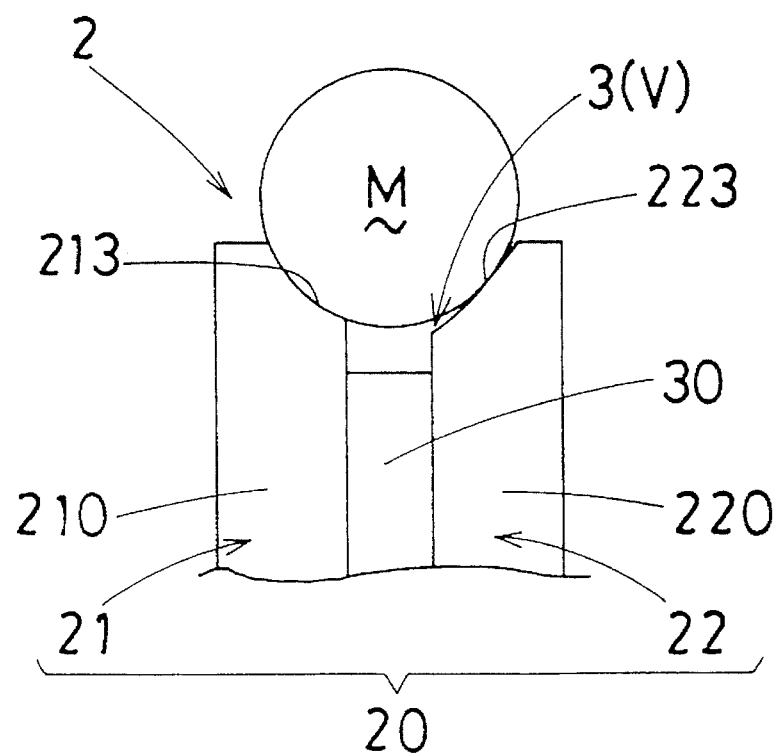
FIG. 15 is an essential front view showing a different embodiment of the invention.

What is shown in FIG. 15 is a compound type of the embodiment shown in FIG. 13 and the embodiment shown in FIG. 14. That is, one of the abutting surfaces 213, 223 is formed completely along the spherical matter M, but the other is formed in an arc (in sectional view) not completely formed along the spherical matter M. Thus, the invention may be also realized if the rotary parts 210, 220 of the first support 21 and second support 22 are not formed symmetrically.

Figure 16:
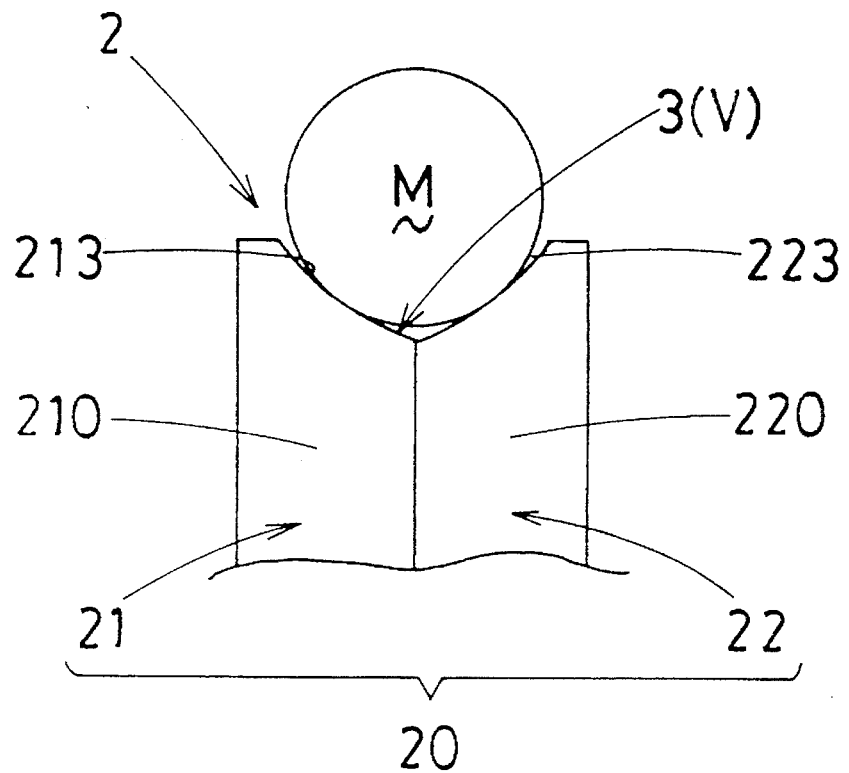
FIG. 16 is an essential front view showing a different embodiment of the invention.

As shown in FIG. 16, relating to the embodiment in FIG. 14, whether in type A or in type B, the constitution of spacer 30 and others is not employed, that is, a wide interval is not provided between the first support 21 and the second support 22.

Figure 17:
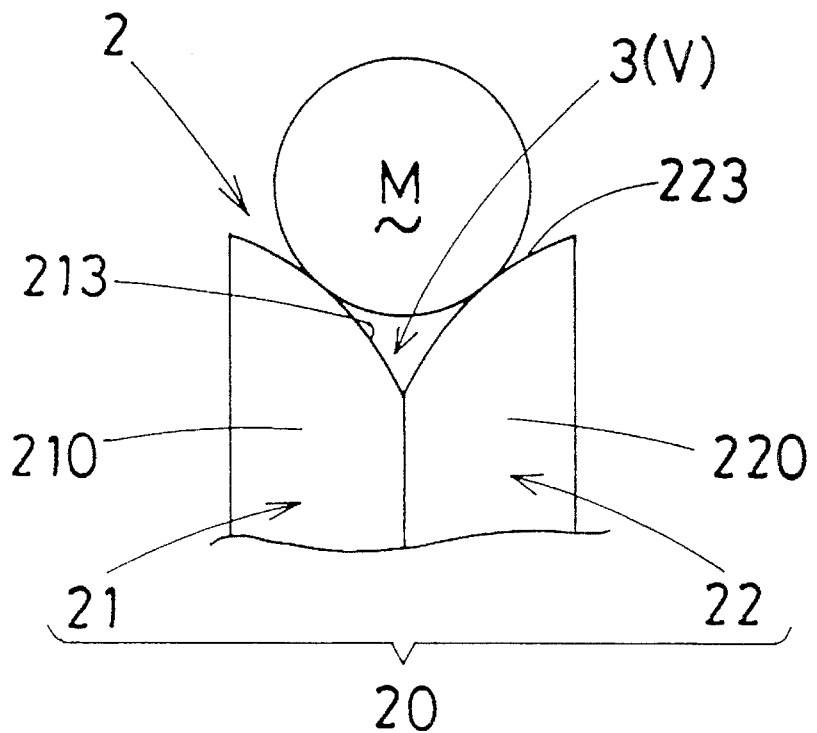
FIG. 17 is an essential front view showing a different embodiment of the invention.

In FIG. 17, the abutting surfaces 213, 223 have a convex curvature on the outside. This embodiment, same as shown in FIG. 16, does not have the spacer 30 and wide gap between the first support 21 and second support 22, but aside from this, it is also possible to realize a constitution having a proper gap between the first support 21 and second support 22 by using spacer 30 or other means mentioned above.

Figure 18:
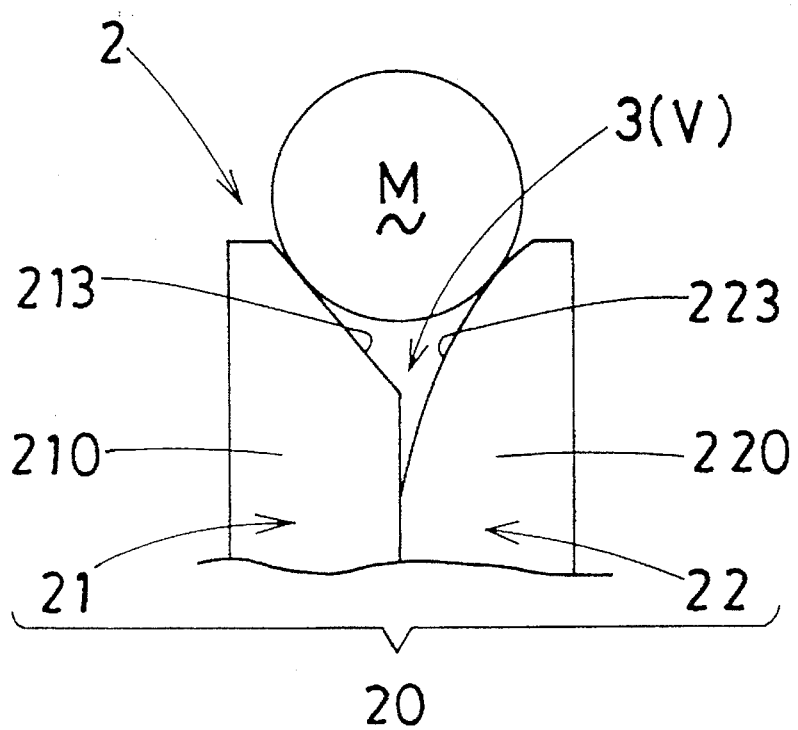
FIG. 18 is an essential front view showing a different embodiment of the invention.

In the embodiment shown in FIG. 18, the first support 21 and second support 22 are a combination of different shapes.

FIG. 18 presents a combination of FIG. 12 and FIG. 17, but other different shapes may be also combined.

Furthermore, the first support 21 and second support 22 may differ in the diameter of rotation (or maximum outside diameter in standing still) or thickness (the lateral direction in FIG. 12 to FIG. 18).

Figure 19:
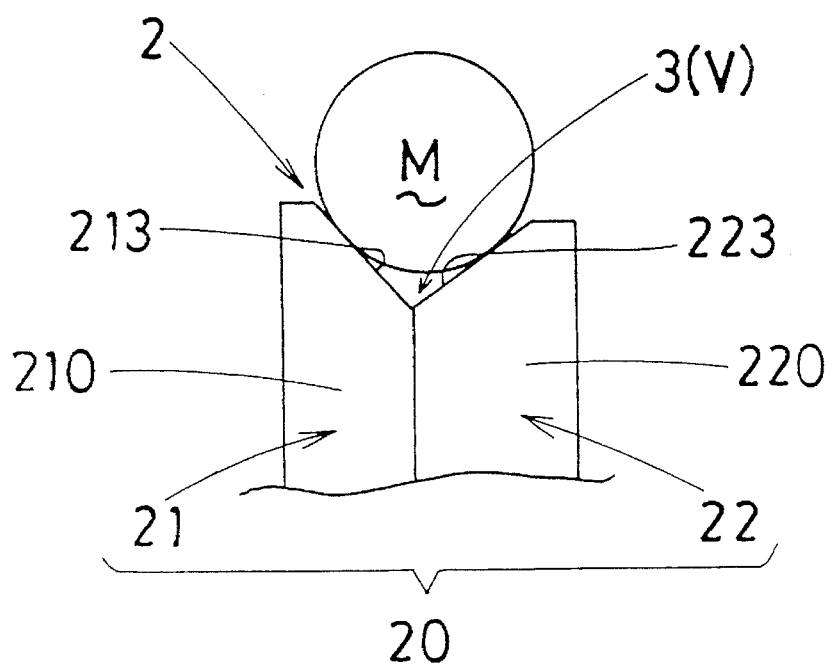
FIG. 19 is an essential front view showing a different embodiment of the invention.

For example, in FIG. 19, similar to the embodiment in FIG. 12, the outside diameter and width of the first support 21 and second support 22 are different. By such difference, as shown in the drawing, the slope angles of the abutting surfaces 213, 213 differ in the first support 21 and second support 22.

Figure 20:
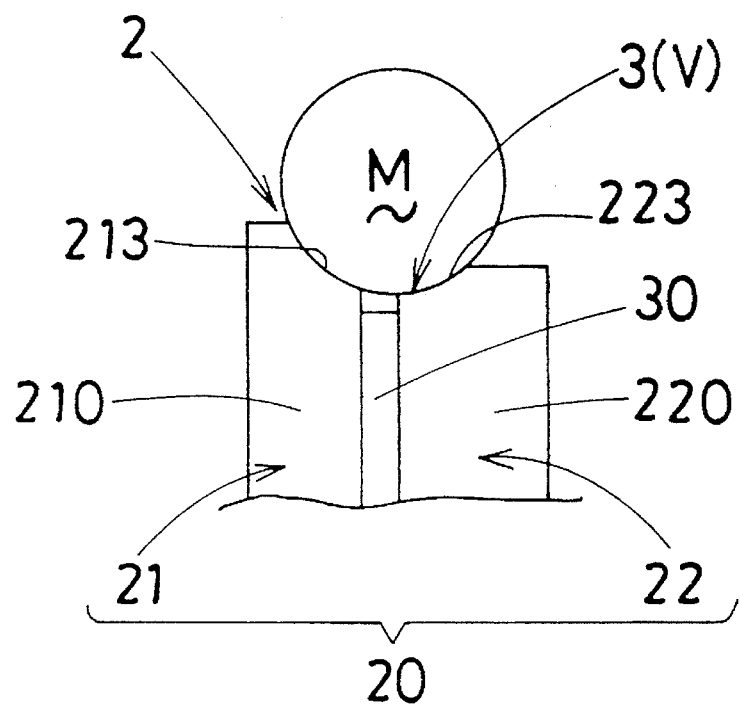
FIG. 20 is an essential front view showing a different embodiment of the invention.

In FIG. 20, similar to the embodiment in FIG. 13, the first support 21 and second support 22 differ in the diameter of rotation (or maximum outside diameter in standing still) and thickness (lateral width in drawing).

Figure 21:
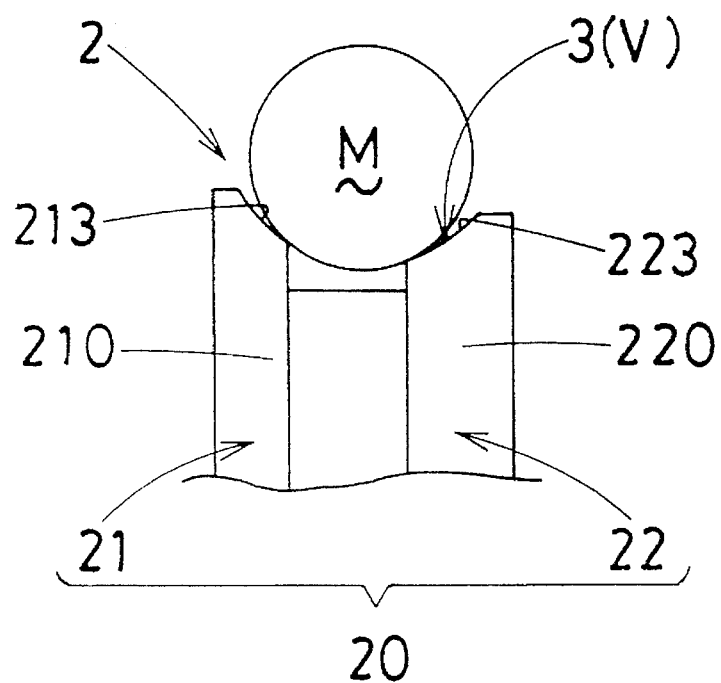
FIG. 21 is an essential front view showing a different embodiment of the invention.

In FIG. 21, similar to the embodiment in FIG. 14, the first support 21 and second support 22 differ in the diameter of rotation (or maximum outside diameter in standing still) and thickness (lateral width in drawing).

Figure 22:
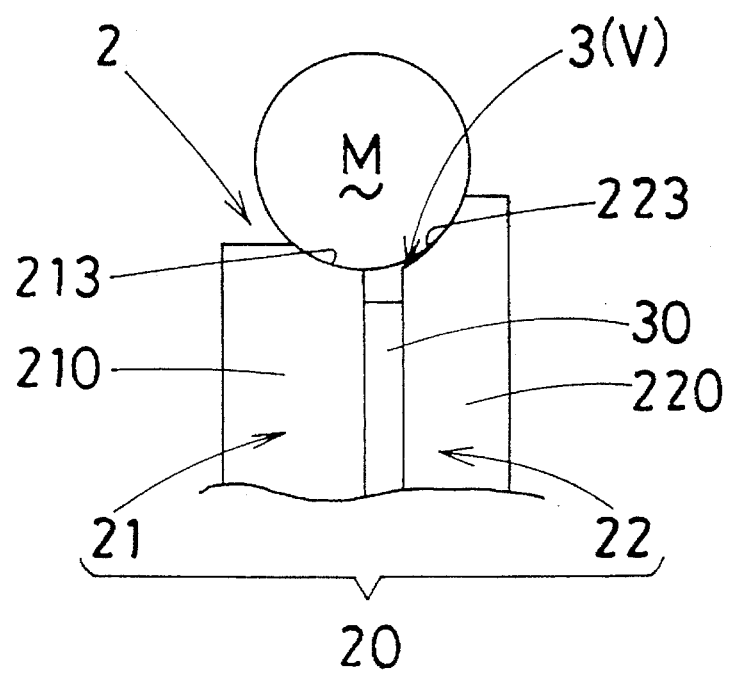
FIG. 22 is an essential front view showing a different embodiment of the invention.

In FIG. 22, similar to the embodiment in FIG. 15, the first support 21 and second support 22 differ in the diameter of rotation (or maximum outside diameter in standing still) and thickness (lateral width in drawing).

Figure 23:
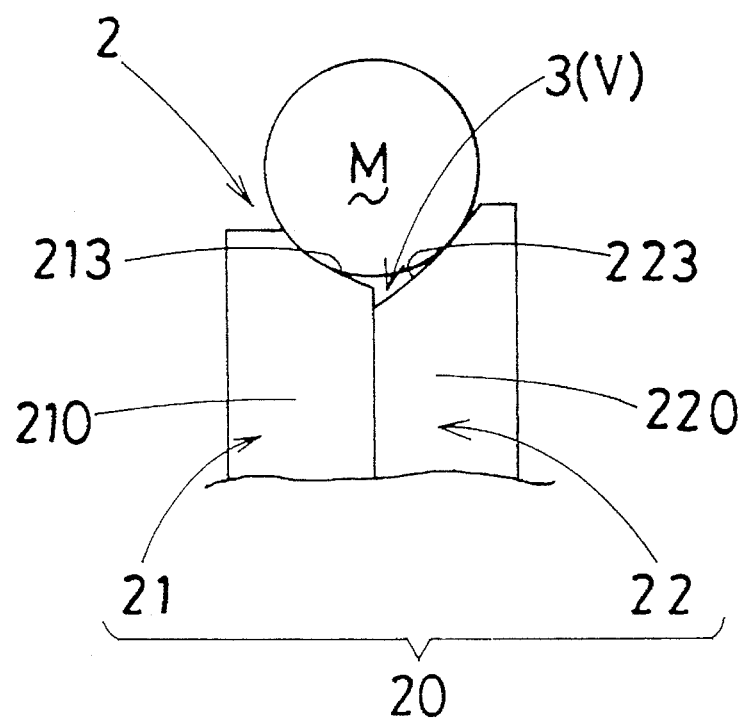
FIG. 23 is an essential front view showing a different embodiment of the invention.

In FIG. 23, moreover, similar to the embodiment in FIG. 16, the first support 21 and second support 22 differ in the diameter of rotation (or maximum outside diameter in standing still). In this embodiment, the thickness (lateral width in drawing) of the first support 21 and second support 22 is nearly equal, but it is realized if the thickness is also different.

Figure 24:
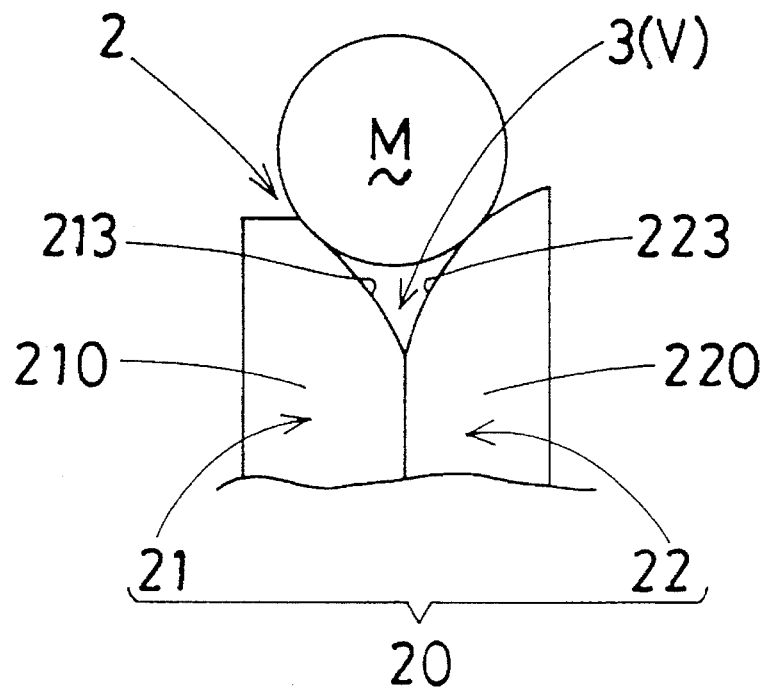
FIG. 24 is an essential front view showing a different embodiment of the invention.

In FIG. 24, similar to the embodiment in FIG. 17, the first support 21 and second support 22 differ in the diameter of rotation (or maximum outside diameter in standing still) and thickness (lateral width in drawing).

Figure 25:
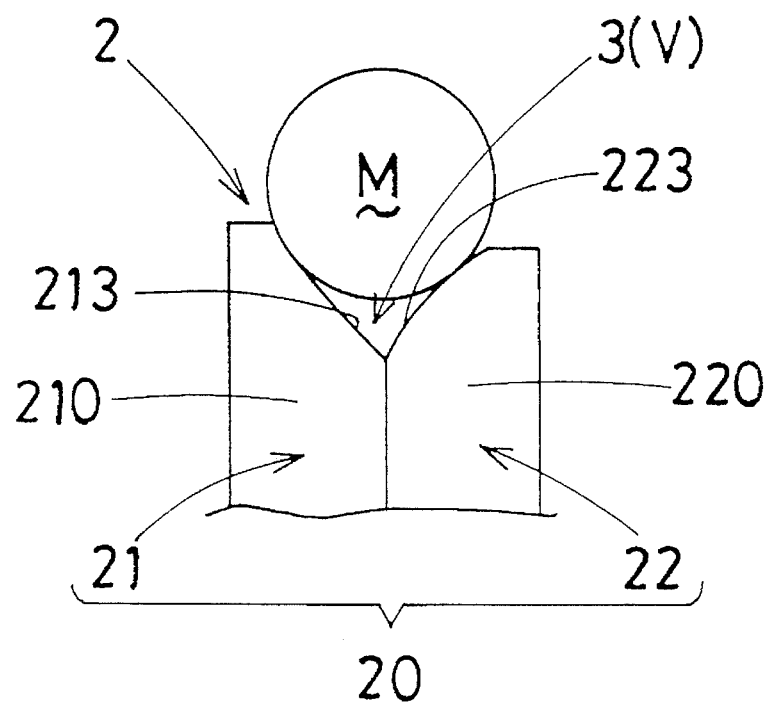
FIG. 25 is an essential front view showing a different embodiment of the invention.

In FIG. 25, moreover, similar to the embodiment in FIG. 18, the first support 21 and second support 22 differ in the diameter of rotation (or maximum outside diameter in standing still). In this embodiment, the thickness (lateral width in drawing) of the first support 21 and second support 22 is nearly equal, but it is realized if the thickness is also different.

As mentioned above, the embodiments in FIG. 12 to FIG. 25 can be realized whether in type A or in type B.

In the above embodiments having such constitutions, supply of spherical matter M to be inspected, sorting depending on the result of inspection, and other steps in a series can be completely automated.

That is, as shown in FIG. 3, a feed unit 4 for accommodating the spherical matters M to be inspected is provided, and a guide 40 for sending the spherical matters M sequentially from the bottom of the feed unit 4 to the holder 2 is provided in the feed unit 4. The inspection unit 1 projects light from the projector 11 to the surface of the spherical matter M sent to the holder 2 automatically from the feed unit 4 by the guide 40, and receives the reflected light in the receiver 12. The result is sent to the photo sensor array 13. The auxiliary support 23 has its rear end fixed to the other end, and when the inspection is over, the front end is lifted upward, and the spherical matter M is released and dropped into the sorting unit 5.

The sorting unit 5 detects by the photo sensor array 13, and sorts the spherical matter M on the basis of the data of approval or rejection sent to the integrated circuit 14. The sorting unit 5 is realized by an existing device.

For example, the sorting unit 5 constitutes a branched passage as shown in FIG. 3, and a rejected spherical matter M as a result of inspection is sent into one passage 51, and an approved spherical matter M is sent into the other passage 52. In this way, the sorting unit 5 sorts out the individual spherical matters M according to approval or rejected as judged by the inspection unit 1. In this embodiment, in both passages 51, 52, it is appropriate to form a lid for closing one passage and opening the other passage depending on approval or rejection of the spherical matter M sent in one passage, at the branching position.

In the embodiment shown in FIG. 3, the constituent members such as sensor 10 and holder 2 are placed in liquid E for the purpose of inspection, but it is also possible to inspect by placing in gas or in vacuum. The liquid E is not limited in kind, and inspection may be done in oil, water-soluble rust preventive, or other liquid.

The constitution in FIG. 5 in which the auxiliary support 23 has a rotating body 230 to apply torque independently from the other support to the spherical matter M may be also realized in FIG. 6 through FIG. 9, and in such a case, the first support 21 and second support 22 may be constituted as shown in FIG. 12 through FIG. 25.

Figure 27:
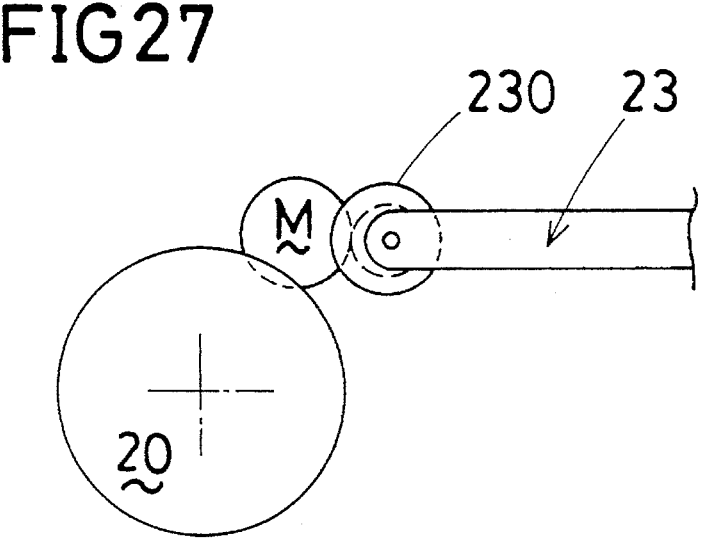
FIG. 27 is an essential schematic side view of the above embodiment.
Figure 26:
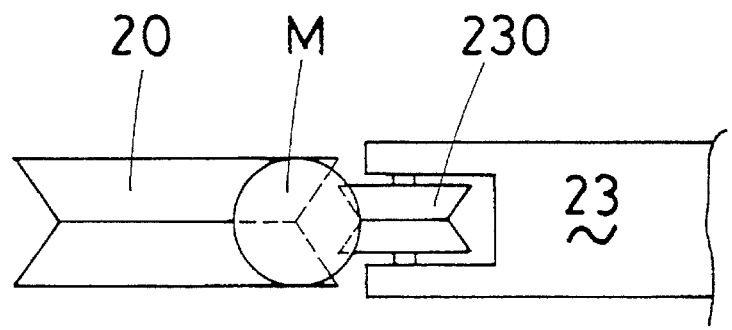
FIG. 26 is an essential schematic plan view showing a different embodiment of the invention.

The auxiliary support 23 may be also constituted, for example, as shown in FIG. 26 and FIG. 27, to have the rotating body 230 in the same shape as the support 20 (or the first support 21 and second support 22). Therefore, the rotating body 230 may be similar in shape or constitution to the support 20 shown in FIG. 1 and FIG. 2 or FIG. 10 through FIG. 25, or the first support 21 and second support 22 in FIG. 6 through FIG. 9 or FIG. 12 through FIG. 25. Furthermore, the rotating body 230 is not limited to the arrangement in the same direction as the support 20 or first support 21 and second support 22, and while having the same or similar shape as the support 20 or other, it may also possess a rotary shaft at right angle to the rotary shaft of the support 20 or the like, same as the embodiment shown in FIG. 5.

Incidentally, the rotating body 230 may rotate independently by receiving supply of torque from outside (not shown) same as in the embodiment shown in FIG. 5, but without having the own rotating mechanism, it may be designed to be rotated along with rotation of the spherical matter M to support the spherical matter M auxiliarily. Besides, the structure for supporting the rotating body 230 is not limited to the structure shown in the drawing, but a similar structure as in the support 20 or first support 21 and second support 22 may be employed.

Figure 28:
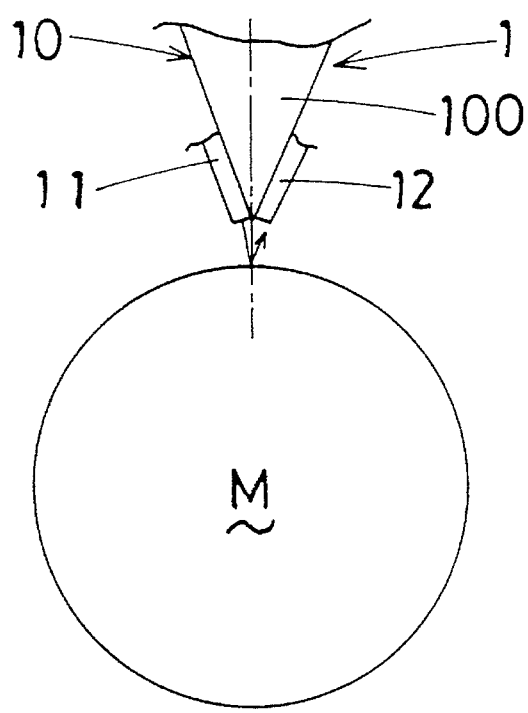
FIG. 28 is an essential side view showing a different embodiment of the invention.

In the photo sensors 10 of the inspection unit 1, the projector 11 and receiver 12 may be held individually, but the projector 11 and receiver 12 may be held together by using a holder 100 of wedge section as shown, for example, in FIG. 28.

Figure 29:
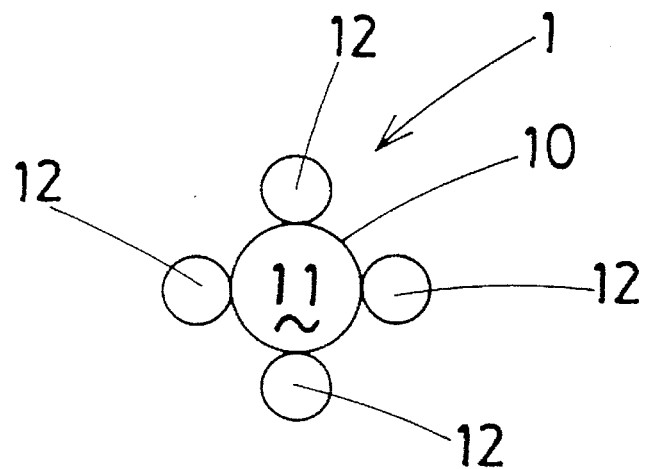
FIG. 29 is an essential schematic bottom view showing a different embodiment of the invention.
Figure 30:
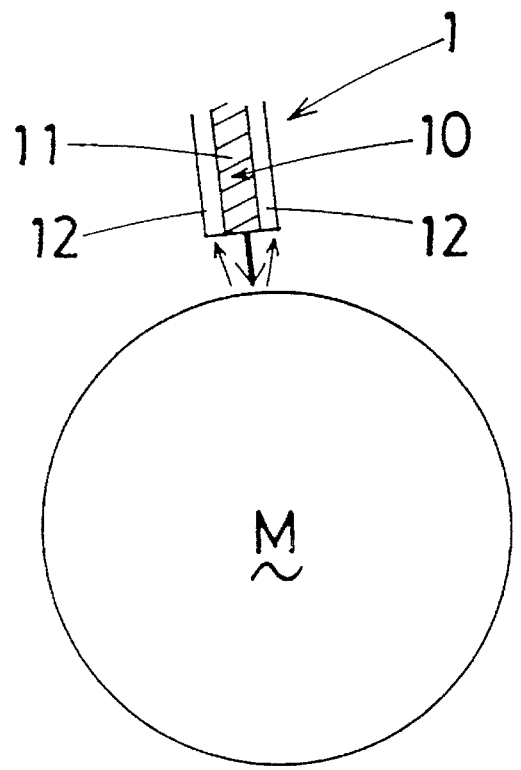
FIG. 30 is an essential schematic side view of the above embodiment.

The photo sensors 10 of the inspection unit 1, not limited to a one-to-one correspondence of the projector 11 and receiver 12, may have a multiple-to-one correspondence. More specifically, for instance as shown in FIG. 29, plural receivers 12 may be disposed around one projector 11. In FIG. 29, incidentally, optical fibers of four receivers 12 are disposed around the optical fiber of the projector 11, but the quantity is not particularly defined, and the embodiment is realized whether the number of optical fibers of the receivers 12 is more than four or not. When the photo sensors 10 . . . shown in FIG. 29 are employed, as shown in FIG. 30, the light emitted by the projector 11 is received individually by the receivers 12.

No matter which type of photo sensors 10 is employed, as shown in FIG. 1 and else, the arrangement of the photo sensors 10 is not limited to a sector layout, and individual photo sensors 10 may be differently configured. When using the photo sensor 10 shown in FIG. 29 and FIG. 30, only one photo sensor 10 is shown in the diagram, but it is not limitative, and a plurality may be disposed. In such a case, too, the configuration of the sensors 10 is free, and they may be disposed at arbitrary positions as required.

In the embodiments in FIGS. 1, 2, 6 to 9, ball bearings are used as bearings 202, 204 and bearings 212, 222, 231, but bearings of other known construction may be also employed (not shown).

Next is described an embodiment of inspection of spherical matter in multiple planes.

Figure 31:
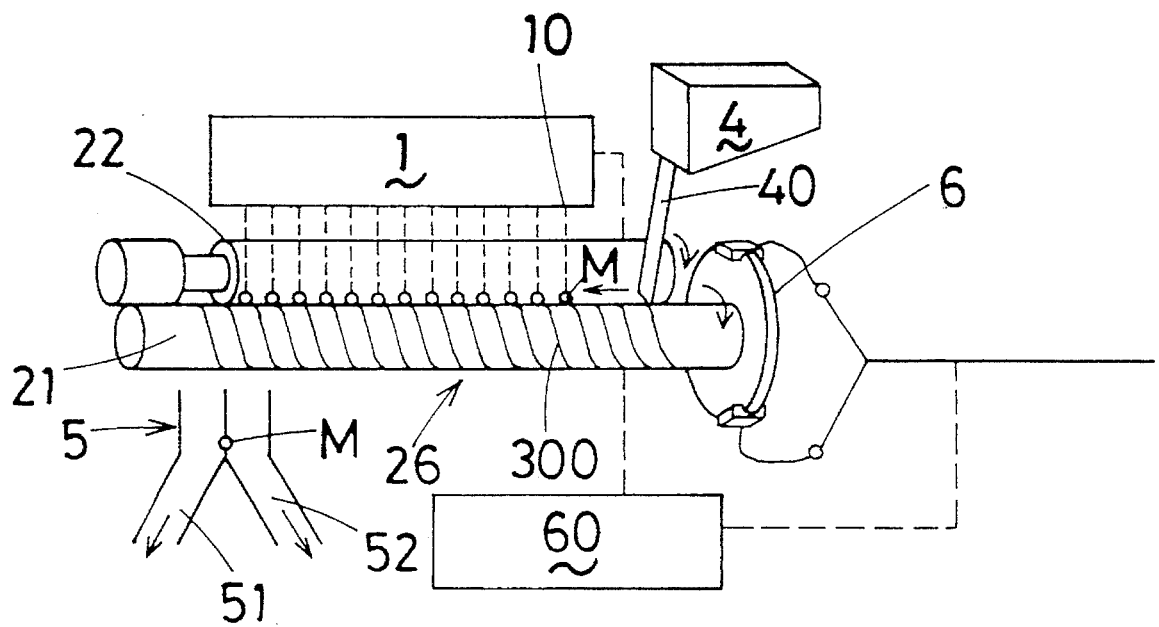
FIG. 31 is a schematic perspective view showing a further different embodiment of the invention.

As shown in FIG. 31, the apparatus comprises a feed unit 4 for feeding spherical matter M such as steel balls, a transfer unit 26 for transferring the spherical matter M supplied from the feed unit 4 for a specific distance, an inspection unit 1 for inspecting the surface of the spherical matter M on the transfer unit 26 by using electromagnetic waves such as rays of light, and a sorting unit 5 for sorting the spherical matter M sent from the transfer unit 26 depending on the result of inspection by the inspection unit 1. The individual constituent elements are sequentially described below.

The feed unit 4 is formed as a hopper for accommodating plural spherical matters M, and is designed to drop the spherical matters M one by one from its bottom to one end of the transfer unit 26. In this embodiment, a guide tube 40 is projecting from the bottom of the feed unit 4 downward to the transfer unit 2 side, and the spherical matter M is guided upward to the transfer unit 26 through the guide tube 40.

The transfer unit 26 is formed by extending a first support 21 of nearly columnar form to form a transfer route of spherical matter M and a second support 22 having at least a nearly same longitudinal width as the first support 21, almost horizontally from the feed unit 4 side to the sorting unit 5 side. In this embodiment, different from the embodiments shown in FIG. 1 through FIG. 30, the first support 21 and second support 22 are formed in a columnar form. Being thus formed, the first support 21 and second support 22 compose a transfer route of the spherical matter M to be mentioned later. The transfer route (the narrow gap 350 mentioned later) formed by these members has a sufficient length for keeping a necessary transfer time for completion of inspection of the spherical matter M by the inspection unit 1 as described below.

Figure 33:
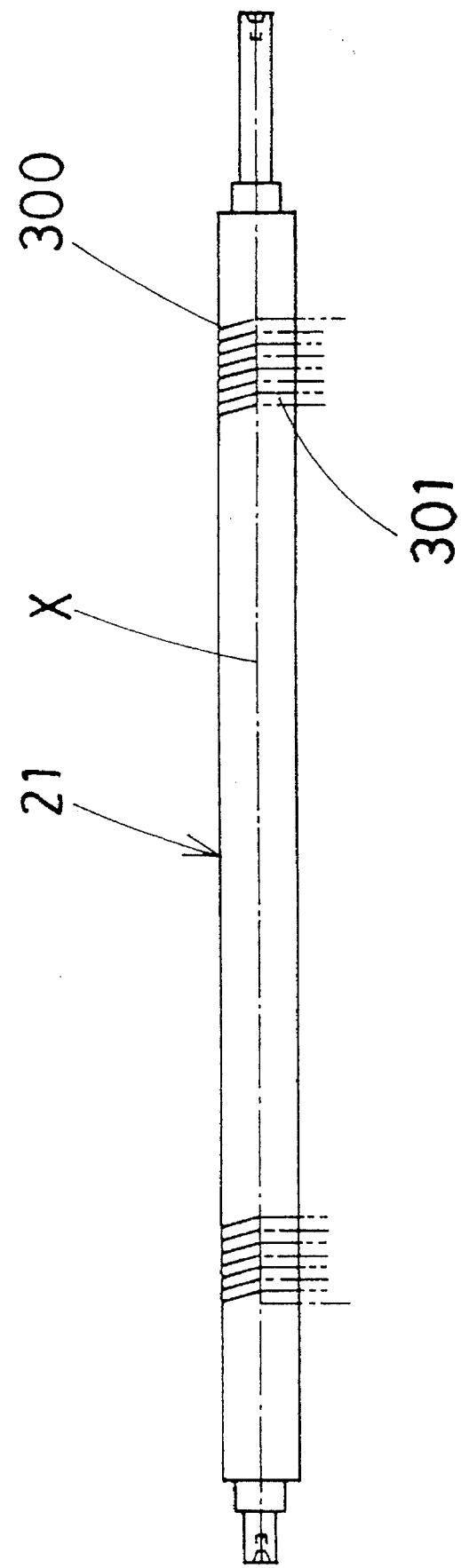
FIG. 33 is an essential front view of the above embodiment of the invention.
Figure 34:
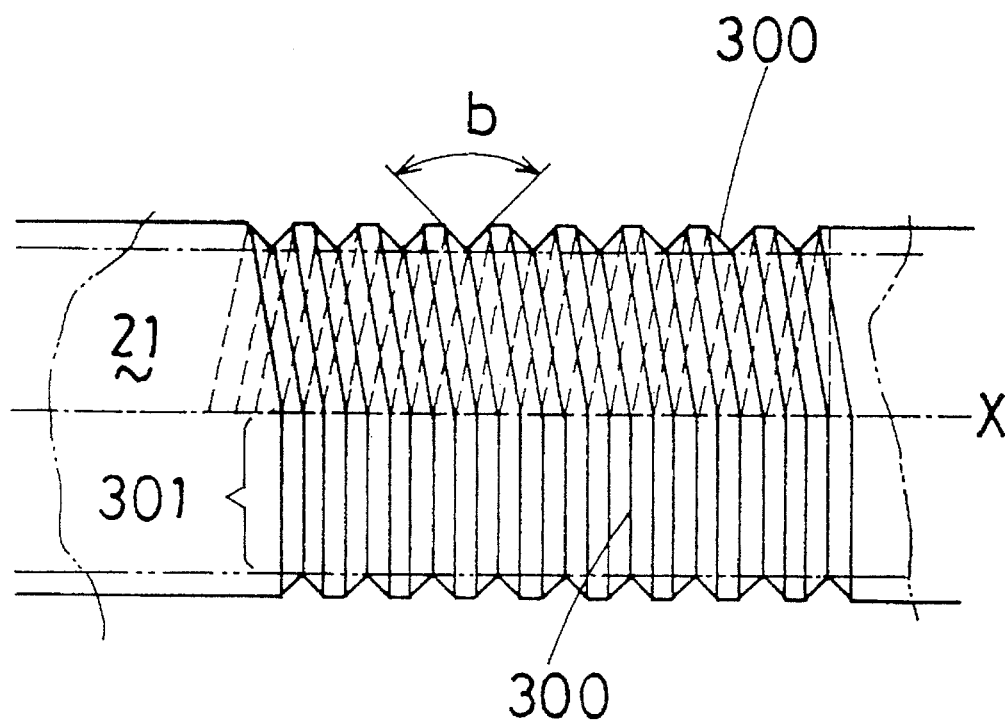
FIG. 34 is an essential front view of the above embodiment of the invention.

In the first support 21, as shown in FIG. 33 and FIG. 34, a guide groove 300 extending spirally from the end of the feed unit 4 side to the end of the sorting unit 5 side is formed on the outer circumference. That is, a spiral groove such as the worm of worm gear is formed.

Figure 32:
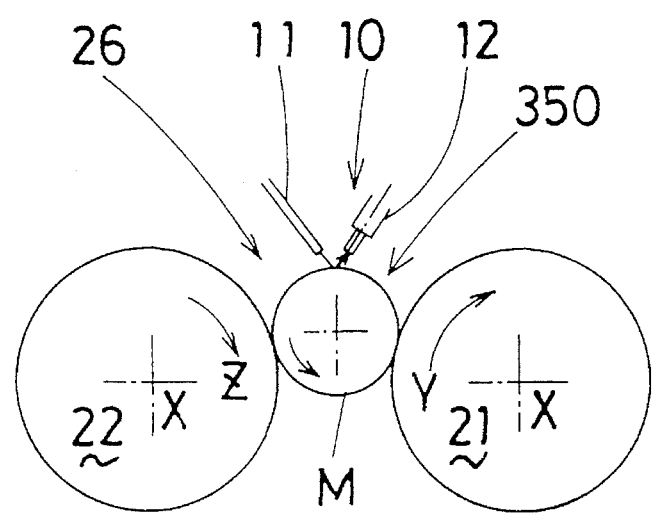
FIG. 32 is an essential schematic sectional view of the above embodiment of the invention.

The first support 21 rotates about the symmetrical axis X (virtual line) of the column formed by itself (FIG. 32). Rotating means such as motor for transmitting its torque to the first support 21 is omitted in order to avoid complication of the drawing.

The guide groove 300 transfers and guides the spherical matter M from the end of the feed unit 4 side to the end of the sorting unit 5 side by the rotation of the first support 21, and sequentially changes the rotating direction of the spherical matter itself in the process of transfer. In the guide groove 300, moreover, plural transfer rest positions 301 of which lead angle is almost zero are formed. The spiral of this guide groove 300 may be either clockwise or counterclockwise, or may be twin spiral (double spiral), and the shown example is not limitative. However, considering the relation with the rotating direction of the first support 21 and rotating direction and configuration of the second support 22, it must be set so that the spherical matter M may be sent from the feed unit 4 to the sorting unit 5. In the spiral of the guide groove 300 shown herein, the lead angle is uniform in other parts than the transfer rest positions 301, but the embodiment is realized also if the lead angle differs depending on the position of the spiral guide groove 300.

Figure 35:
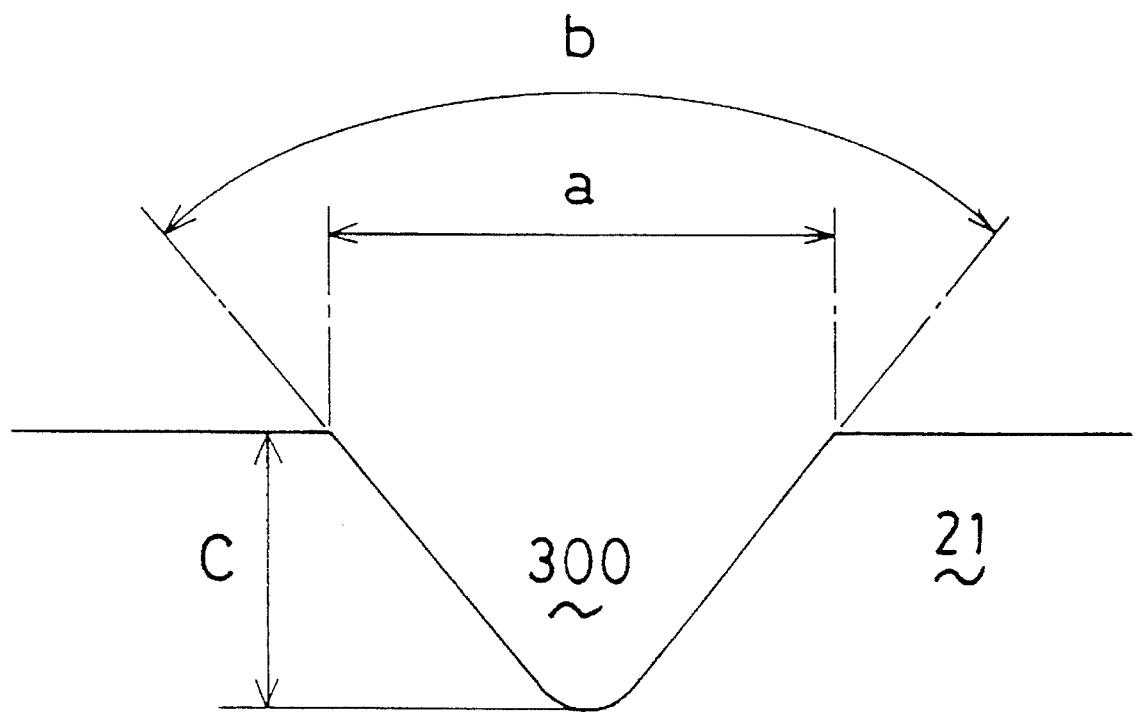
FIG. 35 is an essential explanatory diagram of the above embodiment of the invention.

The interval of adjacent guide grooves 300, the groove width a of the guide groove 300 shown in FIG. 35 (about 80 degrees in the diagram), and the angle b and depth c of cut may be set properly according to the size of the spherical matter M to be transferred. Similarly, the outside diameter of the first support 21 may be set properly depending on the size of the spherical matter M to be transferred.

The second support 22 is, as shown in FIG. 32, nearly of columnar form same as the first support 21, and is disposed almost parallel adjacently to the first support 21, thereby forming a narrow gap 350 against the first support 21. This narrow gap 350 is to prevent the spherical matter M mounted upward from dropping down. Therefore, this narrow gap 350 may be also set according to the size of the spherical matter M to be inspected.

In this embodiment, the second support is also designed to rotate, same as the first support 21, about the own symmetric axis X. In the shown embodiment, the second support 22 is always rotating, but if not necessary, such rotating structure is not required. The shape of the second support 22 is not limited to the columnar form, and it may be formed, for example, as a wall along the first support 21, or in other form than columnar form. Moreover, with the first support 21 and transfer rest position 301 coinciding in location, the second support 22 may be formed in a columnar form having a guide groove with a reverse lead angle (not shown).

By mounting the spherical matter M in the narrow gap 350 as transfer route, the spherical matter in the midst of transfer is supported by making use of the force of the spherical matter M in a direction of dropping into the narrow gap 350. As shown in FIG. 32, the first support 21 rotates in the Y-direction and the second support 22 rotates in the Z-direction. Receiving such torque, the spherical matter M rotates, and advances through the narrow gap 305 toward the sorting unit 5 side.

This forward move of the spherical matter M is effected by the guidance of the guide groove 300. More specifically, a part of the spherical matter M gets into the guide groove 300, and the spherical matter M advances along the guide groove 300 sequentially dislocated by the rotation of the first support 21. While moving, the spherical matter M gets into the section of transfer rest position 301 of the guide groove 300 and is defined by the transfer rest position 301, and in this period, stopping the forward move, the spherical matter M is standing still (in rest state).

The inspection unit 1 possesses plural electromagnetic sensors 10 such as photo sensors, and the individual sensors 10 are disposed along the longitudinal direction of the first support 21 near the first support 21. When using photo sensors as the sensors 10, same as in the foregoing embodiments, the projector 11 and receiver 12 are composed as a pair. In FIG. 32, the projector 11 composed of optical fiber and the receiver 12 are individually provided, but they may be also put in a same unit.

The individual sensors 10 (receivers 12) are designed to judge approval or rejection of spherical matter M depending on the quantity of light reflected from the spherical matter M by projecting light.

More specifically, if there is any defect on the surface of the spherical matter M, part of projected light does not get into the receiver 12, and the quantity of light received by the receiver 12 is decreased from the quantity received from the surface of intact spherical matter M. More precisely, the result of judgement can be confirmed by the lamp of the panel 130 mentioned later, and is finally reflected in sorting by the sorting unit 5.

The sensors 10 are disposed at proper mutual intervals, project light to the surface of the spherical matter M standing still at the individual transfer rest positions 301 of the guide groove 300, and receive the reflected light to inspect the surface of the spherical matter M, thereby detecting flaw, distortion or other defect.

In the embodiment shown in FIG. 31, about twelve sensors 10 are disposed, but the quantity is not limitative, and the embodiment is realized whether greater or smaller than the shown number (however, for the purpose of the invention, at least three pieces should be provided).

Having such constitution, while moving from one sensor to other sensor 10, the spherical matter M is changed in direction sequentially and uniformly by the spiral guide groove 300, thereby avoiding the inspection on the same specific circumference only by all sensors 10 (lowering the probability of such bias or duplication of inspection positions), so that one spherical matter M can be inspected from different direction and at multiple angles by the sensors 10.

Numeral 6 in FIG. 31 shows a position detection device, of which data is sent to an integrated circuit 60 to control the rotation of the first support 21 or second support 22 if necessary to be tuned between the sensors 10 of the inspection unit 3 and the transferred spherical matter M. For example, if necessary, when the spherical matter M gets into the transfer rest position 301 where sensors 10 are located, the rotation of the first support 21 is stopped, or reduced in speed.

The sorting unit 5 composes a branched passage also in this embodiment as shown in FIG. 31, and the spherical matter M rejected as a result of inspection is sent into one branched passage 51, and the approved spherical matter M is sent into the other passage 52. In this way, the sorting unit 5 judges individual spherical matters M according to the inspection result obtained from the inspection unit 1, and sorts out. In this embodiment, too, the passages 51, 52 are selected by a lid which opens one passage and closes the other depending on the approval or rejection of the spherical matter M transferred by placing it at the branching position, or they may be also selected by other known means.

In such constitution, the spherical matter M is sent from the feed unit 5 to the transfer unit 26 sequentially, and multiple spherical matters M can be inspected automatically. At this time, plural spherical matters M are mounted in a row on the transfer unit 26, and therefore means for specifying a defective spherical matter M is needed.

As such specifying means, for example, a device having twelve sensors 10 may be used, in which twelve data receivers (not shown) corresponding one to one to the individual sensors 10 are provided in the inspection unit 1. For example, if a defect (or abnormality) is detected in the fifth sensor 10 from the feed unit 4 side, the information is sent to the data receivers of the sixth and subsequent sensors 10, so that it is known in which sensor 10 the defective spherical matter M is now passing. When the defective spherical matter M has passed the final sensor 10, it is treated as rejection in the sorting unit 4 by the data of the data receiver of the final sensor 10. Alternatively, when any sensor 10 detects a defect, the number of revolutions required for the first support 21 from that sensor 10 position to reach the final sensor 10 position or the front end of the first support 21 may be preliminarily input in the control means so as to control accordingly.

It is also effective to have the following constitution so that the transfer state of spherical matter M having defect may be recognized also from outside.

Figure 36:
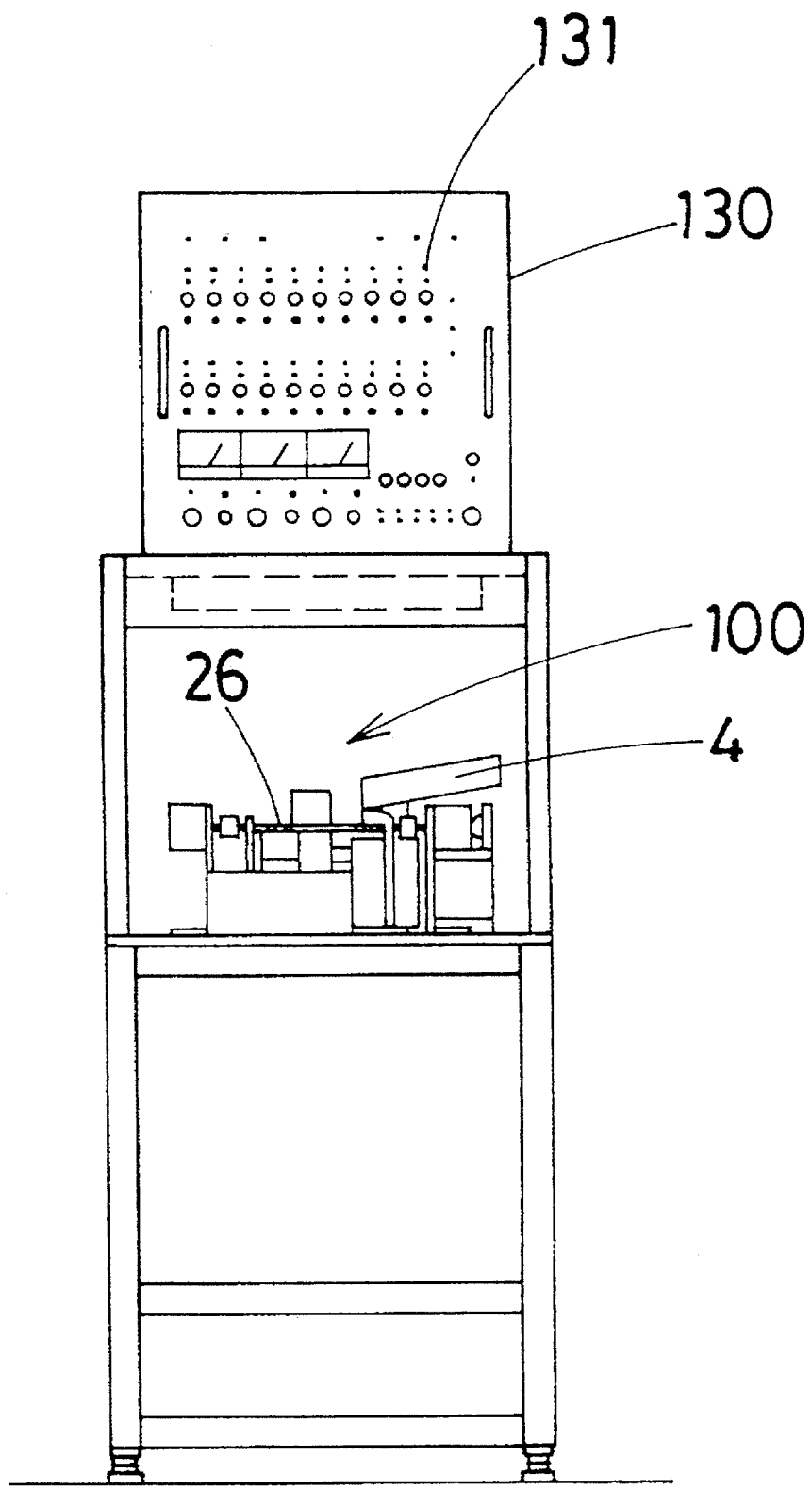
FIG. 36 is a general front view of the above embodiment of the invention.

More specifically, as shown in FIG. 36, a display panel 130 is provided near a device main body 100 comprising feed unit 4, transfer unit 26, inspection unit 1 and sorting unit 5, and lamps 131 corresponding to individual sensors 10 are incorporated in the display panel 130.

In this constitution, for example, when a defect is detected by the fifth sensor 10, the lamp 131 corresponding to this sensor 10 lights up, and as the spherical matter m passes sequentially, the lamps 131 . . . corresponding to the sensors 10 light up successively, so that the defective spherical matter M can be easily recognized from outside.

In the embodiment explained so far, the device main body 100 comprising feed unit 4, transfer unit 26, inspection unit 1 and sorting unit 5 is usually placed in the atmosphere (air), but it may be also placed in other ambient conditions. For example, it may be used in other gas than air, in vacuum or even in liquid.

If used in liquid, the kind of liquid is not specified, including oil, water-soluble rust preventive, and other liquids.

By the first embodiment, the direction of the spherical matter may be automatically changed relatively to the sensor, and the surface of a great number of spherical matters can be inspected efficiently and precisely.

By the second embodiment, in addition to the effects of the first invention, plural positions on the surface of one spherical matter can be securely inspected, and defects can be detected thoroughly, and the qualification as product can be sorted at high precision.

By the third embodiment, plural positions on the surface of one spherical matter can be securely inspected, and defects can be detected thoroughly, and the qualification as product can be sorted at high precision.

By the fourth embodiment, in addition to the effects of the third invention, a finer adjustment is possible, and more precise inspection is realized.

By the fifth embodiment, by the preliminary move in the preliminary section of the transfer unit, plural positions of the surface of spherical matter can be securely inspected, and defects can be inspected thoroughly, so that the qualification as product can be sorted at high precision.

What is claimed is:

1. A surface inspection apparatus of spherical matter comprising:

an inspection unit possessing electromagnetic sensors such as photo sensors, and a holder for mounting steel balls or other spherical matter, wherein:

the inspection unit detects surface defects of spherical matter put on the holder by said electromagnetic sensors, the holder possesses a rotatable support and an auxiliary support for supporting the spherical matter together with the support, the support possesses a receiving groove formed in an annular form along its rotating peripheral surface, said receiving groove accommodating the vicinity of the bottom of the spherical matter, and the spherical matter is rolled within the receiving groove by the rotation of the support, so that the direction of the spherical matter can be changed, and the auxiliary support is formed separately from the support, and disposed near the support, and is designed to support the portion of the spherical matter exposed from the receiving groove, and holding the spherical matter at a specific position.

2. The surface inspection apparatus of spherical matter as claimed in claim 1, wherein the auxiliary support possesses a rotating body in the position contacting with the spherical matter, said rotating body rotating the spherical body in a different direction from the rotating direction of the support.

3. The surface inspection apparatus of spherical matter comprising:

an inspection unit possessing electromagnetic sensors such as photo sensors, and a holder for mounting steel balls or other spherical matter, wherein:

the inspection unit detects surface defects of spherical matter put on the holder by said electromagnetic sensors, the holder possesses a rotatable first support, a rotatable second support, and an auxiliary support for supporting the spherical matter together with the first support and second support, and the first support and second support can rotate at mutually different rotating speeds.

4. The surface inspection apparatus of spherical matter as claimed in claim 3, wherein the auxiliary support possesses a rotating body at a position contacting with the spherical matter, and the rotating body provides the spherical matter with a torque in a proper direction.

* * * * *